US006852546B1

(12) United States Patent
Brown

(10) Patent No.: US 6,852,546 B1
(45) Date of Patent: Feb. 8, 2005

(54) DIAGNOSIS OF AUTOIMMUNE DISEASE

(75) Inventor: James L. Brown, Athens, OH (US)

(73) Assignee: Diagnostic Hybrids, Inc., Athens, OH (US)

( * ) Notice: Subject to any disclaimer, the term of this patent is extended or adjusted under 35 U.S.C. 154(b) by 0 days.

(21) Appl. No.: 09/539,735

(22) Filed: Mar. 30, 2000

(51) Int. Cl.$^7$ ............................................. G01N 33/564

(52) U.S. Cl. ..................... 436/506; 436/507; 435/7.21; 435/29

(58) Field of Search ................................ 436/506, 507; 435/7.21, 29

(56) References Cited

U.S. PATENT DOCUMENTS

| | | | |
|---|---|---|---|
| 4,608,341 A | 8/1986 | Ambesi-Impiombato | |
| 4,609,622 A | 9/1986 | Kohn et al. | |
| 5,071,773 A | 12/1991 | Evans et al. | |
| 5,401,629 A | 3/1995 | Harpold et al. | |
| 5,436,128 A | 7/1995 | Harpold et al. | |
| 5,814,461 A | 9/1998 | Bergmann et al. | ........... 435/7.1 |

OTHER PUBLICATIONS

Akamizu et al. "Cloning chromosomal assignment, and regulation of the rat thyrotropin receptor: Expression of the gene is regulated by thyrotropin, agents that increase cAMP: levels, and thyroid autoantibodies." Proc. Natl. Acad. Sci. USA 87:5677–5681 (1990).

Saji et al. "Increases in cytosolic Ca$^{++}$ down regulate thyrotropin receptor gene expression by a mechanism different from the cAMP signal," Biochem. Biophys. Res. Commun. 176:94–101 (1991).

Saji et al. "Regulation of thyrotropin receptor gene expression in rat FRTL–5 thyroid cells," Endocrinology 130:520–523 (1992 a).

Saji et al., "Hormonal regulation of major histocompatibility complex class I genes in rat thyroid FRTL–5 cells: Thyroid–stimulating hormone induces a cAMP–mediated decrease in class I expression," Proc. Natl. Acad. Sci. USA 89:1944–1948 (1992 b).

Ikuyama et al., "Characterization of the 5'–flanking region of the rat thyrotropin receptor gene," Mol. Endocrinol. 6:793–804 (1992 a).

Ikuyama et al. "Role of the cyclic adenosine 3',5'–monophosphate response element in efficient expression of the rat thyrotropin receptor promoter," Mol. Endocrinol. 6:1701–1715 (1992 b).

Shimura et al. "The cAMP response element in the rat thyrotropin receptor promoter," J. Biol. Chem. 268:24125–24137 (1993).

Shimura et al. "Thyroid–specific expression and cyclic adenosine 3', 5'–monophosphate autoregulation of the thyrotropin receptor gene involves thyroid transcription factor–1," Mol. Endocrinol. 8:1049–1069 (1994).

Saji et al. "Regulation of major histocompatibility complex class I gene expression in thyroid cells," J. Biol. Chem. 272:20096–20107 (1997).

Kirshner et al. "Major histocompatibility class I gene transcription in thyrocytes: a series of interacting regulatory DNA sequence elements mediate thyrotrophin/cyclic–adenosine 3',5'–monophosphate repression," Mol. Endocrinol. 14:82–98 (2000).

Brivanlou and Darnell, Jr., "Signal transduction and the control of gene expression," Science 295 813–818 2002.

Di Cerbo et al. (1999) "Signaling pathways involved in thyroid hyperfunction and growth in Graves' disease," Biochimie 81:415–24.

Taskén et al. (2004) "Localized Effects of cAMP Mediated by Distinct Routes of Protein Kinase A," Physiol. Rev. 84:137–167.

Saji et al. (1991) "Insulin and Insulin–Like Growth Factor–I Inhibit Thyrotropin–Increased Iodide Transport in Serum–Depleted FRTL–5 Rat Thyroid Cells: Modulation of Adenosine 3',5'–Monophosphate Signal Action," Endocrinology 128:1136–1143.

Khan et al. (1995) "Arachidonic Acid and Free Fatty Acids as Second Messengers and the Role of Protein Kinase C," Cell. Signal, 7:171–184.

Leemhius et al. (2002) "The Protein Kinase A Inhibitor H89 Acts on Cell Morphology by Inhibiting Rho Kinase.," J. Pharmacol. Exp. Ther. 300:1000–1007.

Davies et al. (2000) "Specificity and mechanism of action of some commonly used protein kinase inhibitors," Biochem. J. 351:95–105.

Cross et al. (1995) "Wortmannin and Its Structural Analogue Demethoxyviridin Inhibit Stimulated Phospholipase A$_2$ Activity in Swiss 3T3 cells Wortmannin Is Not a Specific Inhibitor of Phosphatidylinositol 3–kinase," J. Biol. Chem. 270:25352–25355.

Vlahos et al. (1994) "A Specific Inhibitor of Phospatidylinositol 3–Kinase, 2–(4–Morpholinyl)–8–phenyl–4H–I–benzopyran–4–one (LY2294002)," J. Biol. Chem. 269:5241–5248.

Garcia et al. (2002) "PI3K is Involved in the IGF–I Inhibition of TSH–Induced Sodium/Iodide Symporter Gene Expression," Mol. Endocrinol. 16: 342–352.

(List continued on next page.)

Primary Examiner—Patrick J. Nolan
(74) Attorney, Agent, or Firm—Medlen & Carroll, LLP

(57) ABSTRACT

The present invention provides methods and compositions useful in the diagnosis and management of autoimmune diseases. In particular, the present invention provides improved methods and compositions for the diagnosis and management of Graves' disease. The methods of the present invention avoid the need for radioactivity and are much simpler, economical, and rapid than methods traditionally used for the diagnosis of Graves' disease.

32 Claims, 7 Drawing Sheets

OTHER PUBLICATIONS

Marocci et al. (1987) "Norepinephrine and Thyrotropin Stimulation of Iodide. Efflux in FRTL–5 Thyroid Cells Involves Metabolites of Arachidonic Acid and is Associated with the iodination of thyroglobulin," Endocrinology 120:1127–1133.

Kohn et al. (1997) "Characterization of Monoclonal Thyroid Stimulating and Thyrotropin Binding–Inhibiting Autoantibodies from a Hashimoto's Patient Whose Children had Intrauterine and Neonatal Thyroid Disease," J. Clin. Endocrinol. Metab., 82:3998–4009.

Sarlis, et al. (1997) "Graves' Disease Following Thyrotoxic Painless Thyroiditis. Analysis of Antibody Activates Against Thyrotropin Receptor in Two Cases," Thyroid 7:829–836.

Wortsman et al. (1998) "Thyrotropin Receptor Epitopes Recognized by Graves' Autoantibodies Developing under Immunosuppressive Therapy," J. Clin. Endocrinol. Metab. 83:2302–2308.

Adams et al. "The Assessment of Thyroid Function by Tracer Tests with Radioactive Iodine," New Zealand Med. J., pp 36–41.

McKenzie (1958) "The Bioassay of Thyrotropin in Serum," Endocrinol. 372–382.

Kriss et al. (1964) "Isolation and Identification of the Long–Acting Thyroid Stimulator and Its Regulation to Hyperthyroidism and Circumscribed Pretibial Myxedema," J. Clin. Endo. and Metab. 24:1005–1028.

Inui et al. (1998) "Increase of Thyroid Stimulating Activity in Graves' Immunoglobulin–G by High Polyethylene Glycol Concentrations Using Porcine Thyroid Cell Assay," Thyroid 8:319–325.

Minich et al. (2004) "A Coated Tube Assay for the Detection of Blocking Thyrotropin Receptor Autoantibodies," J. Clin. Endocr. Metab. 89:352–356.

Davies et al. (1998) "Thyroid Stimulating Antibodies Predict Hyperthyroidism," J. Clin. Endocr. Metab. 83:3777–3781.

Dumont et al. (2002) "Cross signalling, cell specificity, and physiology," AJP 283(1):C2–C28.

Kimura et al. (2001) "Regulation of thyroid cell proliferation by TSH and other factors: A critical evaluation of in vitro models," Endocrine Review 22(5):631–656.

Bell et al. (2002) "TSH signaling and cell survival in 3T3–L1 preadipocytes," AJP 283(4):C1056–1064.

Kohn et al. (1995) "The Thyrotropin Receptor," Vitamins and Hormones 50:287–384.

Damante and Di Lauro (1994) "Thyroid–specific gene expression," Biochem Biophys Acta 1218:255–266.

Czech (2000) "PIP2 and PIP3: Complex Roles at the Cell Surface," Cell 100:603–606.

Botero and Brown (1998) "Bioassay of thyrotropin receptor antibodies with Chinese hamster ovary cells transfected with recombinant human thyrotropin receptor: Clinical utility in children and adolescents with Graves disease," J. Pediatr. 132:612–618.

Federman in *Scientific American Medicine,* Scientific American, New York, NY, Dale and Federman (eds.), 1997, Chptr. 3, Section I, pp. 2–22.

Baldet et al. (1987) "Thyroid stimulating antibody: an index of thyroid stimulation in Graves' disease?" Acta Endocrinol. (Copenh) 116:7–12.

Rapoport et al. (1984) "Clinical Expression with a Human Thyroid Cell Bioassay for Thyroid–Stimulating Immunoglobulin," J. Clin. Endocrinol. Metab. 58:332–338.

Yokoyama et al. (1987) "Heterogeneity of Graves' Immunoglobulin G: comparison of Thyrotropin Receptor Antibodies in Serum and in Culture Supernatants of Lymphocytes Transformed by Epstein–Barr Virus Infection," J. Clin. Endocrinol. Metabol. 64:215–218.

McKenzie and Zakarija (1989) "Clinical Review 3, The Clinical Use of Thyrotropin Receptor Antibody Measurements," J. Clin. Endocrinol. Metabol. 69:1093–1096.

Kasagi et al. (1986) "A Sensitive and Practical Assay for Thyroid–Stimulating Antibodies Using Crude Immunoglobulin Fractions Precipitated with Polyethylene Glycol," J. Clin. Endocrinol. Metabol. 62:855–862.

Bidey et al. (1985) "Characterization of thyroid–stimulating immunoglobulin–induced cyclic AMP accumulation in the rat thyroid cell strain FRTL–5: potentiation by forskolin and calibration against reference preparations of thyrotrophin," J. Endocrinol. 105:7–15.

Michelangeli et al. (1994) "Measurement of thyroid stimulating immunoglobulins in a new cell line transfected with a functional human TSH receptor (JP09 cells), compared with an assay using FRTL–5 cells," Clin. Endocrinol. 40:645–652.

Kakinuma et al.(1997) "The Human Thyrotropin (TSH) Receptor in a TSH Binding Inhibition Assay for TSH Receptor Autoantibodies," J. Clin. Endocrinol. Metabol. 82:2129–2134.

Vitti et al. (1993) "Detection of Thyroid–Stimulating Antibody Using Chinese Hamster Ovary Cells Transfected with Cloned Human Thyrotropin Receptor," J. Clin. Endocrinol. Metabol. 76:499–503.

Kosugi et al. (1989) "Mechanisms by Which Low Salt Condition Increases Sensitivity of Thyroid Stimulating Antibody Assay," Endocrinol. 25:410–417.

Evans et al. (1999) "Development of a Luminescent Bioassay for Thyroid Stimulating Antibodies," J. Clin. Endocrinol. Metabol. 83:374.

Maniatis et al. (1987) "Regulation of Inducible and Tissue–Specific Gene Expression," Science 236:1237–1245.

Voss et al. (1987) "The role of enhancers in the regulation of cell–type–specific transcriptional control," Trends Biochem. Sci. 11:287–289.

Dijkema et al. (1985) "Cloning and expression of the chromosomal immune interferon gene of the rat," EMBO J. 4:761–767.

Uetsuki et al. (1989) "Isolation and Characterizationof the Human Chromosomal Gene for Polypeptide Chain Elongation Factor–$1\alpha$," J. Biol. Chem. 264:5791–5798.

Kim et al. (1990) "Use of human elongation factor $1\alpha$ as a versatile and efficient expression system," Gene 91:217–223.

Mizushima and Nagata (1990) "pEF–BOS, a powerful mammalian expression vector," Nuc. Acids Res. 18:5322.

Gorman et al. (1982) "The Rous sarcoma virus long terminal repeat is a strong promoter when introduced into a variety of eukaryotic cells by DNA–mediated transfection," Proc. Natl. Acad. Sci. USA 79:6777–6781.

Boshart et al. (1985) "A Very Strong Enhancer is Located Upstream of am Immediate Early Gene of Human Cytomegalovirus," Cell 41:521–530.

Sambrook et al., Molecular Cloning: A Laboratory Manual, 2nd ed., Cold Spring Harbor Laboratory Press, New York [1989], pp. 16.7–16.8.

Sambrook et al., Molecular Cloning: A Laboratory Manual, 2nd ed., Cold Spring Harbor Laboratory Press, New York [1989], pp. 16.9–16.15.

Chiovato et al. (1994) "Detection of antibodies blocking thyrotropin effect using Chinese hamster ovary cells transfected with the cloned human TSH receptor," J. Endocrinol. Invest. 717:809–816.

Di Cerbo et al. (1999) "Graves' Immunoglobulins Activate Phospholipase $A_2$ by Recognizing Specific Epitopes on Thyrotropin Receptor," J. Clin. Endocrinol. Metabol. 84:3283.

Guyton (1981) "The Thyroid Hormones," in *Textbook of Medical Physiology*, Sixth Edition, W.B. Saunders Company.

Hartmann et al. (1993) "The Effects of PEG on Second Antibody Immunoprecipitation and Its Use in Immunoassay," J. Immuno. 14:241–266.

Jacobson et al. (1997) "Epidemiology and Estimated Population Burden of Selected Autoimmune Diseases in the United States," Clin. Immunol. and Immunop. 83:223–243.

Loos et al. (1995) "Enhanced cAMP accumulation by the human thyrotropin receptor variant with the Pro52Thr substitution in the extracellular domain," Eur. J. Biochem. 232:62 (Abstract).

Ludgate et al. (1990) "Use of the recombinant human thyrotropin receptor (TSH–R) expressed in mammalian cell lines to assay TSH–R autoantibodies," Mol. and Cell. Endocrinol. 73:R13–R18.

Ludgate et al. (1992) "Recombinant TSH–Receptor for Determination of TSH–Receptor Antibodies," Exp. Clin. Endocrinol. 100:73–74.

McKenzie and Zakarija (1985) "Assays of Thyroid–Stimulating Antibody," Methods in Enzymol. 109:677–691.

Morgenthaler et al. (1998) "Application of a bioassay with CHO cells for the routine detection of stimulating and blocking autoantibodies to the TSH–receptor," Horm. Metab. Res. 30:162, Abstract.

Murakami et al. (1995) "Clinical usefulness of thyroid–stimulating antibody measurement using Chinese hamster ovary cells expressing human thyrotropin receptors," Euro. J. Endocrinol. 133:80–86.

Ochi et al. (1999) "Clinical Usefulness of TSAb Assay with High Polyethylene Glycol Concentrations," Horm. Res. 51:142–149.

Perret et al. (1990) "Stable Expression of the Human TSH Receptor in CHO Cells and Characterization of Differentially Expressing Clones," Biochem. Biophys. Res. Comm. 171:1044–1050.

Persani et al. (1993) "Measurement of cAMP accumulation in Chinese hamster ovary cells transfected with the recombinant human TSH receptor (CHO–R): a new bioassay for human thyrotropin," J. Endocrinol. Invest. 16:511–519.

Roitt et al. (1998) Immunology, Fifth Edition, Mosby International Ltd., pp. 371–380.

Saito et al. (1989) "Enhancement of the Activity of Thyroid–Stimulating Antibodies by Anti–Human IgG Antibodies In Vitro," Clin. Endocrinol. 31:325–334.

Smith et al. (1988) "Autoantibodies to the Thyrotropin Receptor," Endocrine Reviews 9:106–121.

Vitti et al. (1988) "Measurement of TSAb directly in serum using FRTL–5 Cells," J. Endocrinol. Invest. 11:313–317.

Wallaschofski and Peschke (1999) "Detection of thyroid stimulating (TSAB)– and thyrotropin stimulation blocking (TSBAB) antibodies with CHO cell lines expressing different TSH–receptor numbers," Clin. Endocrinol. 50:365–372.

Watson et al. (1998) "A new chemiluminescent assay for the rapid detection of thyroid stimulating antibodies in Graves' disease," Clin. Endo. 49:577–581.

Yamashiro et al. (1999) "Mechanism of the Augmentative Effect of High Polyethylene Glycol (PEG) Concentrations on the Thyroid Stimulating Activity in TSAb–IgG Using a Porcine Thyroid Cell Assay," Endocrine Research 25:67–75.

FAQ Information: FAQ on Graves' Disease (1999) http//www.geocities.com/Athens/3626/graves.html.

FAQ about Graves' Disease (1999) http://www.ngdf.org/faq.htm.

Morgenthaler et al., "Application of a bioassay with CHO cells for the routine detection of stimulating and blocking autoantibodies to the TSH–receptor," *Horm. Metab. Res.* 30:162–168 [1998].

DIAGNOSIS OF AUTOIMMUNE DISEASE

FIELD OF THE INVENTION

The present invention provides methods and compositions useful in the diagnosis of autoimmune diseases. In particular, the present invention provides methods and compositions for use in the diagnosis and management of Graves' disease.

BACKGROUND OF THE INVENTION

Graves' disease (also referred to as "diffuse toxic goiter"), is the leading cause of hyperthyroidism due to the action of autoantibodies that recognize and bind to receptors present on the thyroid gland, resulting in gland growth and overproduction of thyroid hormone. Graves' disease is reported to be the most frequent cause of hyperthyroidism in childhood and adolescence (See, Boter and Brown, J. Pediatr. 132:612–618 [1998]).

Typically, the clinical picture of the disease in young adults is very easily recognized. The patients are more commonly female than male, and report sweating, palpitations, nervousness, irritability, insomnia, tremor, frequent stools, and weight loss in spite of a good appetite. Physical examination usually shows mild proptosis, stare, lid lag, a smooth, diffuse, non-tender goiter, tachycardia (especially after exercise) with loud heart sounds, and often a systolic murmur or left sternal border scratch, tremor, onycholysis, and palmar erythema; often, a bruit is heard over the thyroid, and a cervical hum is almost always present. In patients with these symptoms, Graves' disease is readily recognized, and can be confirmed with laboratory tests (See, Federman, Thyroid, in Dale and Federman (eds.), *Scientific American Medicine*, Scientific American, New York, N.Y., [1997] p. 3:I-6).

Although the signs and symptoms described above can be troublesome, other manifestations of the disease can be more dangerous. One of the most disturbing manifestations is severe exophthalmos, accompanied by ophthalmoplegia, follicular conjunctivitis, chemosis, and loss of vision. Additional manifestations include dermopathy, pretibial myxedema, clubbing, and in the most severe cases, acropachy. These signs and symptoms are indicative of the autoimmune etiology of Graves' disease.

Despite the typical clinical picture of Graves' disease, methods are needed to confirm the diagnosis, as well as provide prognostic indicators for management and treatment. In addition, in cases where the cause of hyperthyroidism is unclear, diagnostic test methods must be utilized to determine the etiology. Although in vivo methods such as radioactive-iodine uptake (RAIU) may be used in the diagnosis and monitoring of patients with Graves' disease (See e.g., Baldet et al., Acta Endocrinol. (Copenh) 116:7–12 [1987]), there are two basic groups of in vitro assay systems developed for this purpose. One is dependent upon the measurement of some index of thyroid stimulation (e.g., cAMP generation) and the other assesses the ability of thyroid-stimulating autoantibodies (TSAb) to inhibit the binding of radiolabelled thyroid stimulating hormone (TSH) to its receptor. These methods include bioassays and in vitro assays for TSAb. However, as recently as 1984, there was no widespread application of methods to measure the thyroid-stimulating immunoglobulin (TSI or TSAb) in Graves' disease diagnosis (See e.g., Rapoport et al., J. Clin. Endocrinol. Metabol., 58:332–338 [1984]). In addition, it was recognized that in the sera of Graves' disease patients there is a heterogenous population of immunoglobulin G (IgG) molecules that recognize the thyroid hormone receptor (See e.g., Yokoyama et al., J. Clin. Endocrinol. Metabol., 64:215–21 [1987]). Further, the recognition that TSH-binding inhibition assays do not necessarily reflect a thyroid-stimulating activity contributed to confusion in attempts to reach agreement on the clinical application of such assays (See e.g., McKenzie and Zakarija, J. Clin. Endocrinol. Metabol., 69:1093–1096 [1989]). Limitations in terms of sensitivity and specificity were also problematic. Indeed, problems associated with available assay systems resulted in arguments that the measurement of thyroid peroxidase antibodies is a sufficiently sensitive marker for underlying thyroid autoimmunity (See, Botero and Brown, supra).

As indicated by Rapoport et al., the available assays that could be performed easily, in a standardized manner, and for large numbers of samples had significant limitations in terms of sensitivity and/or specificity, making these tests unreliable for clinical use. These problems apply primarily to assays that measure the ability of TSI to inhibit the binding of radiolabelled TSH to human thyroid plasma membranes (i.e., the assays do not measure TSI activity per se). Also, not all of the anti-TSH receptor antibodies are stimulatory. Rapoport et al. further indicate that assays using TSI stimulation of adenylate cyclase activity in human thyroid plasma membranes are seriously lacking in sensitivity. Some assays are unpractical for general clinical use, including those that rely upon the use of fresh human thyroid tissue, involve extremely difficult techniques with limited sample capacity, and are very laborious and/or uneconomical (See e.g., Rapoport et al., supra). The development of assays using cultured canine and porcine thyroid cells to measure the cAMP response to TSH were later adapted for use with human thyroid cells which offered potentially superior results. In addition to the requirement for fresh thyroid cells in some of these methods (e.g., the methods discussed by Rapoport et al.), many also required tedious and time-consuming sample preparation prior to assaying the specimens. For example, some protocols require laborious and time-consuming dialysis methods and/or precipitation of immunoglobulins in the test sera with ammonium sulfate or polyethylene glycol (See e.g., Rapoport et al., supra; and Kasagi et al., J. Clin. Endocrinol. Metabol., 62:855–862 [1986]).

In view of the problems encountered with these assay systems, other methods were investigated in an effort to develop an assay that is easy to perform, reliable, sensitive, and specific for Graves' disease autoantibodies. For example, the use of bioassays to measure cAMP production rely upon the use of cells of non-human origin grown in continuous culture or on human cells used as primary cultures or frozen in aliquots for use as needed. Problems with the use of human thyroid cells include the variability in responsiveness of surgically obtained thyroid tissue. Thus, cells of non-human origin gained popularity, including the rat thyroid cell line (FRTL-5). This is a non-transformed, differentiated cell line that has been well-studied and characterized (See e.g., Bidey et al., J. Endocrinol., 105:7–15 [1985]; and Michelangeli et al., Clin. Endocrinol., 40:645–652 [1994]). However, a number of disadvantages make these cells less than ideal for Graves' disease assays. For example, the cells are slow growing and have fastidious growth requirements which include the need for TSH. Consequently, it is necessary to deprive the cells of TSH for at least 5 days prior to assay in order to achieve a reasonable level of sensitivity.

Subsequent development of cells such as the JP09 cells (Chinese hamster ovary cells transfected with a functional human TSH receptor) and other cell lines which stably express the human TSH receptor have greatly improved the assay systems available for the detection of Graves' disease autoantibodies. These cells have a TSH receptor that is comparable to that of native thyrocytes and possess a functional signal transduction system involving G-protein coupling, activation of adenylate cyclase and cAMP generation in response to TSH and to thyroid-stimulating antibodies (TSAb) (See e.g., Michelangeli et al., supra). These cells have been reported to be superior to FRTL-5 cells as they provide similar diagnostic information, but are more sensitive, grow faster, have less fastidious growth requirements, and respond to unextracted sera, in comparison with FRTL-5 cells (Michelangeli et al., supra; see also. Kakinuma et al, J. Clin. Endocrinol. Metabol., 82:212902134 [1997]). In addition, these methods are more rapid and reproducible, and perhaps more specific for detection of human autoantibodies directed against the human receptor. Further, the assays are easier and less cumbersome to perform than those using the FRTL-5 cell line (See e.g., Vitti et al., J. Clin. Endocrinol. Metabol., 76:499–503 [1993]). However, these assays rely upon the use of radioactivity (e.g., in radioimmunoassays) to detect and quantitate cAMP and are as a result, still cumbersome. Although an enzyme-linked immunoassay system (i.e., a non-radioactive method that utilizes an enzyme system for a signal, rather than radioactivity) can be used, what is still needed is an assay system for Graves' disease that is safe, easy to use, sensitive, specific, and cost-effective.

SUMMARY OF THE INVENTION

The present invention provides methods and compositions useful in the diagnosis and management of autoimmune diseases. In particular, the present invention provides methods and compositions for the diagnosis and management of Graves' disease.

In one embodiment, the present invention provides methods for determining the presence of thyroid-stimulating autoantibodies in a test sample, comprising: providing i) a test sample suspected of containing thyroid-stimulating autoantibodies, ii) cultured cells contained within a testing means, and iii) polyethylene glycol; exposing the test sample to the cultured cells and polyethylene glycol under conditions such that thyroid-stimulating antibodies are detectable; and observing for the presence of detectable thyroid-stimulating antibodies. In one preferred embodiment, the cultured cells are selected from the group consisting of FRTL-5 cells, CHO—R cells, and CHO-Rluc cells. In another embodiment, the observing is conducted using a luminometer. In further embodiments, the cAMP concentration is also determined. In yet another embodiment, the methods further comprises a Growth Medium, while in other embodiments, the methods further comprises a Stimulation Medium. In some particularly preferred embodiments, the cultured cells are exposed to the Growth Medium prior to exposure of the test sample. In still further embodiments, the cultured cells are exposed to Stimulation Medium after exposure to the test sample. In other particularly preferred embodiments, the Stimulation Medium comprises polyethylene glycol.

The present invention also provides methods for determining the presence of thyroid-stimulating autoantibodies in a test sample, comprising: providing i) a test sample suspected of containing thyroid-stimulating autoantibodies, ii) cultured cells selected from the group consisting of FRTL-5 cells, CHO—R cells, and CHO-Rluc cells contained within a testing means, and iii) polyethylene glycol; exposing the test sample to the cultured cells and the polyethylene glycol under conditions such that thyroid-stimulating antibodies are detectable; and observing for the presence of detectable thyroid-stimulating antibodies, wherein observing is conducted using a luminometer. In further embodiments, the cAMP concentration is also determined. In some embodiments, the methods further comprise a Growth Medium, while in other embodiments the methods further comprise a Stimulation Medium. In some particularly preferred embodiments, the cultured cells are exposed to the Growth Medium prior to exposure of the test sample. In still other embodiments, the cultured cells are exposed to the Stimulation Medium after exposure to the test sample. In yet other preferred embodiments, the Stimulation Medium comprises polyethylene glycol.

The present invention also provides methods for determining the presence of thyroid-stimulating autoantibodies in a test sample, comprising: providing i) a test sample suspected of containing thyroid-stimulating autoantibodies, ii) cultured cells selected from the group consisting of FRTL-5 cells, CHO—R cells, and CHO-Rluc cells contained within a testing means, iii) Growth Medium, and iv) Stimulation Medium, wherein the Stimulation Medium comprises polyethylene glycol; exposing the cultured cells to Growth Medium to produce grown cells; exposing the test sample to the grown cells and Stimulation Medium under conditions such that thyroid-stimulating antibodies are detectable; and observing for the presence of detectable thyroid-stimulating antibodies, wherein said observing is conducted using a luminometer. In further embodiments, the cAMP concentration is also determined. In a particularly preferred embodiment, the cells are CHO-Rluc cells.

DESCRIPTION OF THE INVENTION

Figure 1:
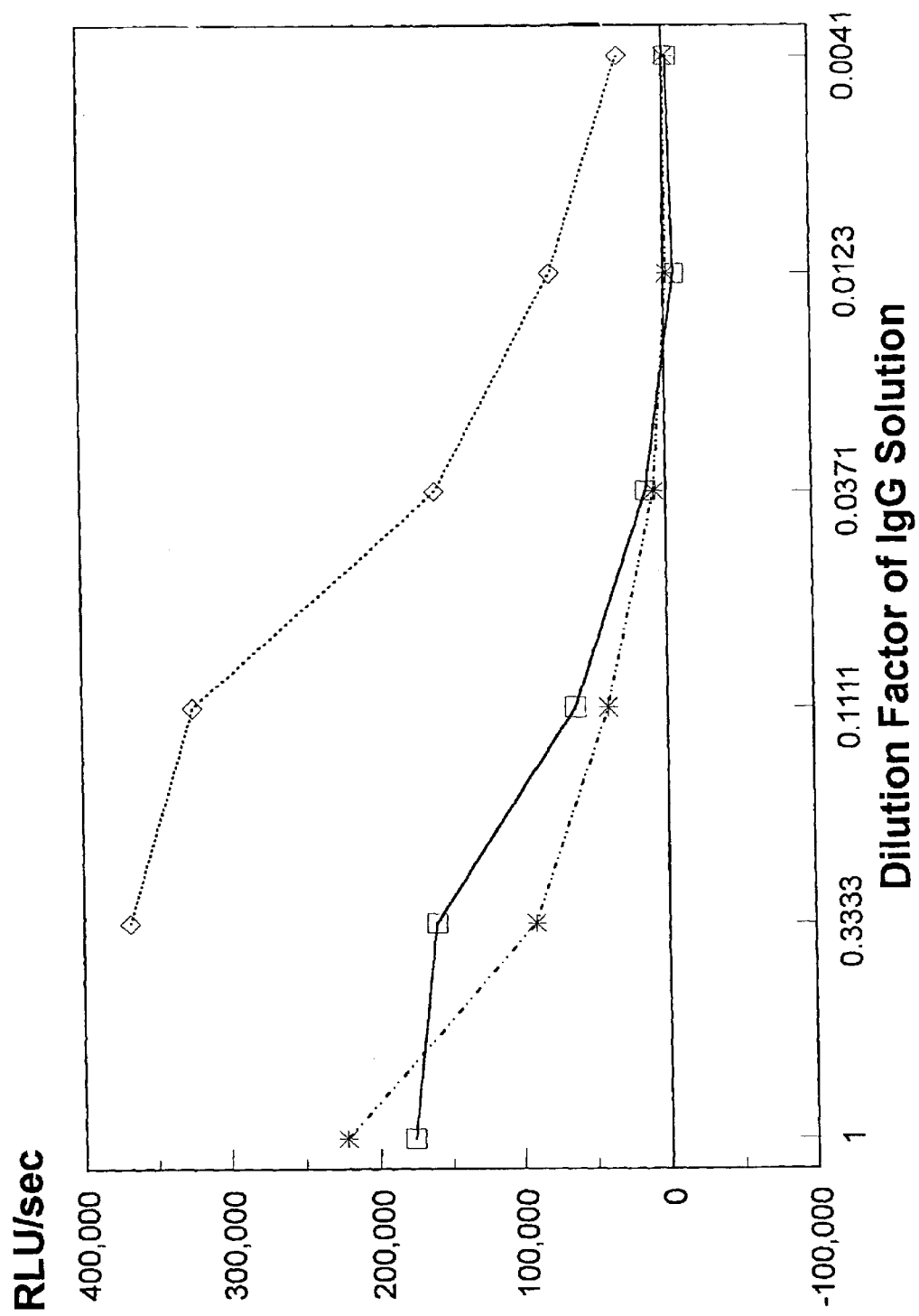
FIG. 1 provides results for serial 3-fold dilutions of three Graves' disease IgG samples (from untreated Graves' patients), in assays utilizing Stimulation Medium containing 6% PEG-8000.

The present invention provides methods and compositions useful in the diagnosis and management of autoimmune diseases. In particular, the present invention provides methods and compositions for the diagnosis and management of Graves' disease. In addition, the present invention provides methods and compositions for monitoring the immune status and responses of individuals. In particular, the present invention finds use in montoring the immune responses of vaccine recipients. The present invention further provides methods and compositions for accelerating and enhancing the attachment of viruses to cell surface receptors, providing increased sensitivity in assays to detect and quantitate viruses in samples.

Diagnosis of Graves Disease

Thyroid-stimulating autoantibodies (TSAb) directed against the thyroid stimulating hormone (TSH) receptor are capable of stimulating thyroid adenylyl cyclase, the enzyme responsible for producing cyclic-adenosine monophosphate (cAMP). These autoantibodies have been used as diagnostic markers for detection and identification of patients suffering from Graves' disease, as these autoantibodies appear to be responsible for the hyperthyroidism seen in patients with this disease.

However, as discussed in more detail below, the methods commonly used to detect and measure these TSAbs are complex and time-consuming. One method utilizes a rat thyroid cell line known as "FRTL-5." This cell line, available from Interthyr Research Foundation (Baltimore, Md.) expresses receptors that cross-react with human TSAbs. In the presence of TSAbs (i.e., upon exposure of the cells to serum from a Graves' patient containing these antibodies), the cells are stimulated to produce cAMP. This cAMP is then measured in a portion of the lysed cells or the medium bathing the cells using a radioimmunoassay method. The FRTL-5 cells formed the basis for the first successful bioassay for the autoantibodies that are pathognomonic of Graves' disease described in U.S. Pat. No. 4,609,622 (herein incorporated by reference). This method soon became the gold standard against which other bioassays were compared.

A typical assay using FRTL-5 cells performed as described by Vitti et al. (Vitti et al., J. Clin. Endocrinol. Metabol., 76:499 [1993]) involves seeding FRTL-5 cells in 96-well plates (30,000 cells/well) in a special complete medium containing 6 hormones (6H) in addition to the normal growth constituents used in cell culture medium. After 2–3 days incubation in a 5% $CO_2$, humidified, 37° C. incubator (i.e., when the cells are confluent), the medium is changed to a "Starvation Medium," which is deficient in TSH (5H), one of the 6 hormones in 6H. The cells are then maintained for 4–5 days in the incubator with a medium change every 2–3 days. During this time the cells do not grow or multiply. The cells are now ready for use in the assay.

The assay is conducted by removing the Starvation Medium and adding a special low sodium chloride, high sucrose buffer (HBSS-NaCl+222 mM sucrose; the formula for this buffer is: 0.0608 g/L $KH_2PO_4$, 0.144 g/L $CaCl_2$, 0.373 g/L KCl, 0.048 g/L $MgSO_4$, 0.097 g/L $Na_2PHO_4$, 1.0 g/L D-glucose, 76 g/L [i.e., 222 mM] sucrose, 4.77 g/L HEPES, and 10 g/L BSA; pH 7.2 to 7.4) containing a phosphodiesterase inhibitor (e.g., 0.5 mM methylisobutyl xanthine), to prevent this enzyme from breaking down cAMP. Specially prepared samples of patient immunoglobulin (IgG), controls, and standards are added to the appropriate wells, usually in triplicate, and the plate is incubated in a 5% $CO_2$, humidified, 37° C. incubator for 2 hours. Following this incubation, 5–10 µL of the medium are removed from each well and used in a radioimmunoassay system to detect the presence of cAMP. Typically this assay is run with about 6 standards in duplicate, with patient and controls also run in duplicate. The assay usually requires an overnight incubation with about an hour required the next day for the separation of free, radiolabelled cAMP from antibody-bound, radiolabelled cAMP.

As the use of radioactivity and long preparation times are negative aspects of the FRTL-5 assay, improved systems have been developed. One investigation involved the use of low salt conditions to increase the sensitivity of the assay system (See, Kosugi et al., Endocrinol., 125:410–417 [1989]). Additional improvements in the bioassay occurred in 1993, with the introduction of a strain of Chinese Hamster Ovary ("CHO") cells transfected with a human TSH receptor ("CHO-R"; See, Vitti et al., supra). This cell line offered two major improvements over the FRTL assay. First, this method involves the use of human TSH receptors instead of rat TSH receptors which should provide greater specificity and perhaps sensitivity for the detection of TSAbs. Second, there is no requirement for the special 6H and 5H medium changes over a 6–8 day period, since the CHO—R cells grow well on a standard supplemented medium and can be used 1–3 days after seeding, depending on the density of the cell suspension used to inoculate the wells. In addition, comparative studies with FRTL-5 cells have shown that the CHO—R cells may be more accurate in detecting Graves' TSAbs (See, Vitti et al.). Nonetheless, the FRTL-5 cells have continued to be the gold standard against which other tests are measured.

A further and more recent improvement was provided by the use of CHO-R cells designed to readily assess the increased amounts of cAMP caused by TSI through the use of a reporter gene's enzyme activity (i.e., luciferase), as described by Evans et al. (Evans et al., J. Clin. Endocrinol. Metabol., 84:374 [1999]). Thus, with the introduction of this engineered cell line (i.e., CHO-Rluc), the complexity and dangers inherent in the use of radioactive compounds used in the previously developed radioimmunoassay for cAMP detection and quantitation are eliminated. With these cells, luciferase is measured simply by removing the medium from the cells, adding a lysis buffer, allowing 20–30 minutes for lysis to occur, removing a sample of the lysate, adding luciferase substrate and measuring light output over a 15 second interval using a luminometer. However, as indicated in the Experimental section below, this method provides equivocal results.

The present invention provides methods that incorporate the advantages of the Evans et al. protocol, while providing additional advantages in terms of reliability and reproducibility. Considerable development effort was dedicated to the development of methods of the present invention, including those that allow the use of CHO-Rluc cells in luminometric assays using TSH and immunoglobulins from untreated Graves' disease patients. The standard protocol originally used involved planting the CHO-Rluc cells from a frozen stock, so as to seed at a concentration that produced confluent monolayers after 18–24 hours of incubation. Initially, the Growth Medium was removed and Stimulation Medium was added to the monolayers, to which a series of TSH standards (e.g., 0, 10, 100, 1000 $\mu$IU TSH/ml), and patient IgG samples were added. As this approach yielded poor results, an overnight starvation or conditioning period was tested. Addition of this step resulted in improved results with lower background values and appeared to be important in producing good values for the TSH standards and the test patient samples. An additional experimental option was also tested in which polyethylene glycol (PEG) was used to enhance antigen and antibody binding. In these experiments, PEG was added to the Stimulation Medium.

In various experiments, different media formulations and combinations were tested, as described in the Experimental section below. For example, starvation with the Stimulation Medium resulted in RLU/sec values of (32,103) for the 0 $\mu$IU/ml TSH standard, −1,148 for the 10 $\mu$IU TSH/ml sample, 47,478 for the 1000 $\mu$IU TSH/ml sample, and 19,350 for IgG sample #13. In this and the following discussions, the numbers in parentheses represent the 0 μIU TSH/ml value, which is subtracted from the values for the standards or samples to yield net values.

Starvation with standard HBSS resulted in RLU/sec values of (21,671) for the 0 μIU/ml TSH control, 1,336 for the 10 uIU TSH/ml sample, 82,466 for the 1000 uIU TSH/ml sample, and 39,082 for IgG sample 413. Starvation with standard HBSS and 6% PEG in the Stimulation Medium resulted in RLU/sec values of (32,562) for the 0 uIU/ml TSH control, 5,980 for the 10 uIU TSH/ml sample, 207,831 for the 1000 uIU TSH/ml sample, and 174,461 for IgG sample #13. Thus, starvation with standard HBSS yielded higher values for TSH and the Graves' disease samples, and the incorporation of PEG into the Stimulation Medium yielded even higher values. These higher values appear to impart a higher level of sensitivity in the methods of the present invention, as compared to other methods. Thus, the present invention provides improvements in ease-of-use and safety of detection methods to diagnose and monitor Graves' disease.

Monitoring of Immune Response Development

As indicated above, the present invention also provides methods and compositions for the monitoring of immune response development. In particular, the present invention provides methods and compositions suitable for monitoring the response of individuals to vaccination. In this embodiment, pre-immune serum (i.e., serum collected prior to administration of vaccine) may be used as a baseline for control purposes. Serum would also be collected shortly following vaccination (e.g., 1–2 weeks after vaccination), as well as periodically in the months following vaccination. The serum samples are then tested for the presence and quantity of neutralizing antibodies. In preferred embodiments, these assays are conducted to monitor the response to viral antigens. In such assays, cells such as ELVIS™ (available from Diagnostic Hybrids, Athens, Ohio) are used in combination with the PEG solution of the present invention. It is contemplated that the use of PEG enhances the antigen-antibody reaction, resulting in higher reactivity in those individuals with anti-viral antibodies.

Definitions

The terms "sample" and "specimen" in the present specification and claims are used in their broadest sense. On the one hand, they are meant to include a specimen or culture. On the other hand, they are meant to include both biological and environmental samples. These terms encompass all types of samples obtained from humans and other animals, including but not limited to, body fluids (e.g., blood), as well as solid tissue.

Biological samples may be animal, including human, fluid or tissue, food products and ingredients such as dairy items, vegetables, meat and meat by-products, and waste. These examples are not to be construed as limiting the sample types applicable to the present invention.

As used herein, the term "kit" is used in reference to a combination of reagents and other materials.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.).

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen (immunogen) or portion of an antigen.

As used herein, the terms "antigen fragment" and "portion of an antigen" are used in reference to a portion of an antigen. Antigen fragments or portions may occur in various sizes, ranging from a small percentage of the entire antigen to a large percentage, but not 100% of the antigen. However, in situations where at least a portion of an antigen is specified, it is contemplated that the entire antigen may be present. It is contemplated that antigen fragments or portions, may, but are not required to comprise and "epitope" recognized by an antibody. Antigen fragments or portions also may or may not be immunogenic.

As used herein, the term "autoantibodies" refers to antibodies that are capable of reacting against an antigenic constituent of an individual's own tissue or cells (e.g., the antibodies recognize and bind to "self" antigens).

As used herein, the term "immunoassay" is used in reference to any method in which antibodies are used in the detection of an antigen. It is contemplated that a range of immunoassay formats be encompassed by this definition, including but not limited to direct immunoassays, indirect immunoassays, and "sandwich" immunoassays." However, it is not intended that the present invention be limited to any particular format. It is contemplated that other formats, including radioimmunoassays (RIA), immunofluorescent assays (IFA), and other assay formats, including, but not limited to, variations on the ELISA, RIA and/or IFA methods will be useful in the method of the present invention.

As used herein, the term "capture antibody" refers to an antibody that is used to bind an antigen and thereby permit the recognition of the antigen by a subsequently applied antibody. For example, the capture antibody may be bound to a microtiter well and serve to bind an antigen of interest present in a sample added to the well. Another antibody (termed the "primary antibody") is then used to bind to the antigen-antibody complex, in effect to form a "sandwich" comprised of antibody-antigen-antibody. Detection of this complex can be performed by several methods. The primary antibody may be prepared with a label such as biotin, an enzyme, a fluorescent marker, or radioactivity, and may be detected directly using this label. Alternatively, a labelled "secondary antibody" or "reporter antibody" which recognizes the primary antibody may be added, forming a complex comprised of antibody-antigen-antibody-antibody. Again, appropriate reporter reagents are then added to detect the labelled antibody. Any number of additional antibodies may be added as desired. These antibodies may also be labelled with a marker, including, but not limited to an enzyme, fluorescent marker, or radioactivity.

As used herein, the term "reporter reagent" or "reporter molecule" is used in reference to compounds which are capable of detecting the presence of antibody bound to antigen. For example, a reporter reagent may be a colorimetric substance attached to an enzymatic substrate. Upon binding of antibody and antigen, the enzyme acts on its substrate and causes the production of a color. Other reporter reagents include, but are not limited to fluorogenic and radioactive compounds or molecules. This definition also encompasses the use of biotin and avidin-based compounds (e.g., including, but not limited to neutravidin and streptavidin) as part of the detection system. In one embodiment of the present invention, biotinylated antibodies may be used in the present invention in conjunction with avidin-coated solid support.

As used herein the term "signal" is used in reference to an indicator that a reaction has occurred, for example, binding of antibody to antigen. It is contemplated that signals in the form of radioactivity, fluorogenic reactions, luminscent and enzymatic reactions will be used with the present invention. The signal may be assessed quantitatively as well as qualitatively.

As used herein, the term "solid support" is used in reference to any solid material to which reagents such as antibodies, antigens, and other compounds may be attached. For example, in the ELISA method, the wells of microtiter plates often provide solid supports. Other examples of solid supports include microscope slides, coverslips, beads, particles, cell culture flasks, as well as many other items.

As used herein, the term "cell staining" is used in reference to methods used to label or stain cells to enhance their visualization. This staining or labelling may be achieved through the use of various compounds, including but not limited to, fluorochromes, enzymes, gold, and iodine. It is contemplated that the definition encompasses such methods as "in situ chromogenic assays," in which a test (i.e., an assay) is conducted on a sample in situ. It is also contemplated that the in situ chromogenic assay will involve the use of an immunoassay (i.e., an ELISA).

As used herein, the term "Growth Medium" refers to a culture medium formulated to contain various growth factors, including but not limited to vitamins, amino acids, co-factors, and any other appropriate nutrients to enhance growth and replication of cells in culture.

As used herein, the term "Stimulation Medium" refers to a medium formulated to be deficient in certain constituents (e.g., sodium chloride), in order to enhance the stimulation of by TSH and/or TSI, thereby increasing the resulting signal (e.g. cAMP and/or luciferase).

As used herein, the term "Starvation Medium" refers to a medium formulated to be deficient in at least one growth factors included in the Growth Medium. In preferred embodiments, this medium contains only the salts and glucose necessary to sustain cells for a short period of time.

As used herein, the term "organism" and "microorganism," are used to refer to any species or type of microorganism, including but not limited to viruses and bacteria, including *rickettsia* and *chlamydia*. Thus, the term encompasses, but is not limited to DNA and RNA viruses, as well as organisms within the orders *Rickettsiales* and *Chlamydiales*.

As used herein, the term "culture," refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal or insect tissue. These cultures may be derived from adults as well as fetal tissue.

As used herein, the term "finite cell lines," refer to cell cultures that are capable of a limited number of population doublings prior to senescence.

As used herein, the term "continuous cell lines," refer to cell cultures that have undergone a "crisis" phase during which a population of cells in a primary or finite cell line apparently ceases to grow, but yet a population of cells emerges with the general characteristics of a reduced cell size, higher growth rate, higher cloning efficiency, increased tumorigenicity, and a variable chromosomal complement. These cells often result from spontaneous transformation in vitro. These cells have an indefinite lifespan.

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the term "hybridomas," refers to cells produced by fusing two cell types together. Commonly used hybridomas include those created by the fusion of antibody-secreting B cells from an immunized animal, with a malignant myeloma cell line capable of indefinite growth in vitro. These cells are cloned and used to prepare monoclonal antibodies.

As used herein, the term "mixed cell culture," refers to a mixture of two types of cells. In some preferred embodiments, the cells are cell lines that are not genetically engineered, while in other preferred embodiments the cells are genetically engineered cell lines. In some embodiments, the one or more of the cell types is re "permissive" (i.e., virus is capable of replication and spread from cell to cell within the culture). The present invention encompasses any combination of cell types suitable for the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

As used herein, the term "suitable for the detection of intracellular parasites," refers to cell cultures that can be successfully used to detect the presence of an intracellular parasite in a sample. In preferred embodiments, the cell cultures are capable of maintaining their susceptibility to infection and/or support replication of the intracellular parasite. It is not intended that the present invention be limited to a particular cell type or intracellular parasite.

As used herein, the term "susceptible to infection" refers to the ability of a cell to become infected with virus or another intracellular organism. Although it encompasses "permissive" infections, it is not intended that the term be so limited, as it is intended that the term encompass circumstances in which a cell is infected, but the organism does not necessarily replicate and/or spread from the infected cell to other cells. The phrase "viral proliferation," as used herein describes the spread or passage of infectious virus from a permissive cell type to additional cells of either a permissive or susceptible character.

As used herein, the terms "monolayer," "monolayer culture," and "monolayer cell culture," refer to cells that have adhered to a substrate and grow in as a layer that is one cell in thickness. Monolayers may be grown in any format, including but not limited to flasks, tubes, coverslips (e.g., shell vials), roller bottles, etc. Cells may also be grown attached to microcarriers, including but not limited to beads.

As used herein, the term "suspension," and "suspension culture," refers to cells that survive and proliferate without being attached to a substrate. Suspension cultures are typically produced using hematopoietic cells, transformed cell lines, and cells from malignant tumors.

As used herein, the terms "culture media," and "cell culture media," refers to media that are suitable to support the growth of cells in vitro (i.e., cell cultures). It is not intended that the term be limited to any particular culture medium. For example, it is intended that the definition encompass outgrowth as well as maintenance media. Indeed, it is intended that the term encompass any culture medium suitable for the growth of the cell cultures of interest.

As used herein, the term "obligate intracellular parasite," (or "obligate intracellular organism) refers to any organism which requires an intracellular environment for its survival and/or replication. Obligate intracellular parasites include viruses, as well as many other organisms, including certain bacteria (e.g., most members of the orders *Rickettsiales* [e.g., *Coxiella*, *Rickettsia* and *Ehrlichia*] and *Chlamydiales* [e.g., *C. trachomatis*, *C. psittaci*], etc). The term "intracellular parasite," refers to any organism that may be found within the cells of a host animal, including but not limited to obligate intracellular parasites briefly described above. For example, intracellular parasites include organisms such as *Brucella, Listeria, Mycobacterium* (e.g., *M. tuberculosis* and *M. leprae*), and *Plasmodium*, as well as *Rochalimea*.

As used herein, the term "antimicrobial," is used in reference to any compound which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

As used herein, the terms "chromogenic compound," and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator," encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator," and "oxidation-reduction indicator," encompasses all compounds commonly used for detection of oxidation/reduction potentials (i.e., "eH") including, but not limited to various types or forms of tetrazolium, resazurin, and methylene blue.

As used herein, the term "inoculating suspension," or "inoculant," is used in reference to a suspension which may be inoculated with organisms to be tested. It is not intended that the term "inoculating suspension," be limited to a particular fluid or liquid substance. For example, inoculating suspensions may be comprised of water, saline, or an aqueous solution. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "primary isolation," refers to the process of culturing organisms directly from a sample. As used herein, the term "isolation," refers to any cultivation of organisms, whether it be primary isolation or any subsequent cultivation, including "passage," or "transfer," of stock cultures of organisms for maintenance and/or use.

As used herein, the term "presumptive diagnosis," refers to a preliminary diagnosis which gives some guidance to the treating physician as to the etiologic organism involved in the patient's disease. Presumptive diagnoses are often based on "presumptive identifications," which as used herein refer to the preliminary identification of a microorganism.

As used herein, the term "definitive diagnosis," is used to refer to a final diagnosis in which the etiologic agent of the patient's disease has been identified. The term "definitive identification" is used in reference to the final identification of an organism to the genus and/or species level.

The term "recombinant DNA molecule," as used herein refers to a DNA molecule which is comprised of segments of DNA joined together by means of molecular biological techniques.

DNA molecules are said to have "5' ends" and "3'ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5'end" if its 5' phosphate is not linked to the 3' oxygen of a mononucleotide pentose ring and as the "3'end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene," refers to a DNA sequence comprising the coding region of a gene or, in other words, the DNA sequence which encodes a gene product. The coding region may be present in either a cDNA or genomic DNA form. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers and/or promoters, splice junctions, intervening sequences, polyadenylation signals, etc. or a combination of both endogenous and exogenous control elements.

The term "transcription unit," as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element," as used herein refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The terms "reporter gene construct," or "reporter gene vector," as used herein refers to a recombinant DNA molecule containing a sequence encoding the product of a reporter gene and appropriate nucleic acid sequences necessary for the expression of the operably linked coding sequence in a particular host organism. Eukaryotic cells are known to utilize promoters, enhancers, and termination and polyadenylation signals.

The term "reporter gene," refers to an oligonucleotide having a sequence encoding a gene product (typically an enzyme) which is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include but are not limited to bacterial genes encoding β-galactosidase (lacZ), the bacterial chloramphenicol acetyltransferase (cat) genes, firefly luciferase genes and genes encoding β-glucuronidase (GUS).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237 [1987]). Promoter and enhancer elements have been isolated from a variety of eukaryotic sources including genes in yeast, insect and mammalian cells and viruses (analogous control elements [i.e., promoters, are also found in prokaryotes]). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 [1986], and Maniatis, et al., supra [1987]). For example, the SV40 early gene enhancer is very active in a wide variety of cell types from many mammalian species and has been widely used for the expression of proteins in mammalian cells (Dijkema, et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]), and the human cytomegalovirus (Boshart et al., Cell 41:521 [1985]).

The term "promoter/enhancer," denotes a segment of DNA which contains sequences capable of providing both promoter and enhancer functions (for example, the long terminal repeats of retroviruses contain both promoter and enhancer functions). The enhancer/promoter may be "endogenous," or "exogenous," or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals," on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site," or "poly A sequence," as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamH/BclI restriction fragment and directs both termination and polyadenylation (Sambrook, supra, at 16.6–16.7). This 237 bp fragment is contained within a 671 bp BamHI/PstI restriction fragment.

The term "genetically engineered cell line," refers to a cell line that contains heterologous DNA introduced into the cell line by means of molecular biological techniques (i.e., recombinant DNA technology).

The term "stable transfection," or "stably transfected," refers to the introduction an d integration of foreign DNA into the genome of the transfected cell. The term "stable transfectant," refers to a cell which has stably integrated foreign DNA into the genomic DNA.

The term "stable transfection" (or "stably transfected"), refers to the introduction and integration of foreign DNA into the genome of the transfected cell. The term "stable transfectant," refers to a cell which has stably integrated foreign DNA into the genomic DNA.

The term "selectable marker," as used herein refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt)

gene which is used in conjunction with hprt cell lines. A review of the use of selectable markers in mammalian cell lines is provided in Sambrook et al., supra at pp. 16.9–16.15.

The terms "nucleic acid molecule encoding," "DNA sequence encoding," and "DNA encoding," refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The terms "confluent" or "confluency" as used herein in reference to an adherent cell line define a condition wherein cells throughout a culture are in contact with each other creating what appears to be a continuous sheet or "monolayer" of cells.

The terms "cytopathic effect" or "CPE" as used herein describe changes in cellular structure (i.e., a pathologic effect) resulting from external agents such viruses. Common cytopathic effects include cell destruction, syncytia (i.e., fused giant cells) formation, cell rounding vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci is initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. Cytopathic effects are readily discernable and distinguishable by those skilled in the art.

The abbreviation "ONPG," represents o-Nitrophenyl-β-D-Galactopyranoside. ONPG is a substrate for the enzyme β-galactosidase (β-gal). The reaction between ONPG and β-gal produces a yellow product which can be quantified spectrophotometrically at 405 nm.

The abbreviation "X-gal," represents the chemical compound 5-bromo-4-chloro-3-indolyl-β-D-galactopyranoside, a substrate for the enzyme β-galactosidase. The reaction between X-gal and β-galactosidase results in the formation of a blue precipitate which is visually discernable.

The term "hybriwix," represents a product of Diagnostic Hybrids, Inc., Athens, Ohio which allows for quantification of certain viral DNA in an infected monolayer of cells by DNA hybridization. "DNA hybridization" is the annealing of two complementary DNA molecules whose base sequences match according to the rules of base pairing. DNA hybridization is used to identify or quantify an unknown or "target" DNA by hybridization to a known DNA or "probe." The probe is typically labeled with a reporter molecule such as $^{125}$I, a radioisotope which can be detected and quantified with a gamma counter.

The phrase "plaque reduction assay," or "PRA," as used herein describes a standard method used to determine efficacy of anti-viral drugs by enumerating a decrease in plaque formation in a cell monolayer exposed to a drug. A "plaque" is a defined area of "CPE." It is usually the result of infection of the cell monolayer with a single infectious virus which then replicates and spreads to adjacent cells of the monolayer. A plaque may also be referred to as a "focus of viral infection."

The term "permissive" as used herein describes the sequence of interactive events between a virus and its putative host cell. The process begins with viral adsorption to the host cell surface and ends with release of infectious virions. A cell is "permissive" if it readily permits the spread of virus to other cells. Many methods are available for the determination of the permissiveness of a given cell line, including, but not limited to plaque reduction assays, comparisons of the production and/or quantitation of viral proteins based on results obtained from gel electrophoresis, relative comparisons using hybridization analysis to analyze DNA or RNA content, etc.

The term "susceptible," as used herein describes the extent that a permissive or non-permissive host cell can adsorb and be penetrated by a virus. A cell line may be susceptible without being permissive in that it can be penetrated but not release virions. A permissive cell line however must be susceptible.

The phrase "seed on," as used herein describes the act of transferring an aqueous solution of suspended cells into a vessel containing cells adhered to a surface, after which the vessel is stored for a sufficient period of time to allow the suspended cells or "seeds" to settle out by gravity and attach in a relatively uniform manner to the adhered cells and become integrated into the final cell monolayer as a mixture. A "mixed cell monolayer," results from the "seed on" process.

The phrase "seed in," as used herein describes the mixing of two or more aqueous solutions of suspended tissue culture cells, each cell suspension having different cellular properties, and transfer of such mixture of cells into a vessel which is stored for a sufficient period of time to allow the suspended cells to settle out by gravity and attach in a relatively uniform manner such that the distribution of any single cell type is indicative of the relative ratio of the cells in the original mixture.

The term "starts," as used herein refers to the reporter cells which represent a primary infection of virus. The virus infects a reporter cell (a genetically engineered cell) and induces the expression of the reporter gene. A reporter cell can be non-permissive (i.e. permissiveness of the reporter cells is not required) and still produce starts.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); 1M (micromolar); N Normal); mol (moles); mmol (millimoles); μmol (micromoles); nmol (nanomoles); g (grams); mg (milligrams); μg (micrograms); ng (nanograms); l or L (liters); ml (milliliters); μl (microliters); uIU or μIU (micro International Units); cm (centimeters); mm (millimeters); μm (micrometers); nm (nanometers); ° C. (degrees Centigrade); sec. or s (second[s]); min. and m (minute[s]); MW (molecular weight); thyroid stimulating hormone or thyrotropin (TSH); bTSH (bovine TSH); TSI (thyroid stimulating immunoglobulin); TSAb (thyroid stimulating antibodies); EDTA (ethylene diamine tetraacetic acid); RLU/sec (relative light units per second); GM or PM (Growth Medium or Planting Medium); SM (Starvation Medium); HBSS (Hank's Balanced Salt Solution); EMEM (Eagle's Minimum Essential Medium); FBS or FCS (fetal bovine serum or fetal calf serum); DMSO (dimethyl sulfoxide); CHO (Chinese hamster ovary cells); CHO-R (CHO cells transfected with the human TSH receptor; CHO- Rluc (CHO—R cells transfected with the cre-luciferase reporter gene complex); Oxoid (Oxoid, Basingstoke, England); BBL (Becton Dickinson Microbiology Systems, Cockeysville, Md.); DIFCO (Difco Laboratories, Detroit, Mich.); U.S. Biochemical (U.S. Biochemical Corp., Cleveland, Ohio); Fisher (Fisher Scientific, Pittsburgh, Pa.); Sigma (Sigma Chemical Co., St. Louis, Mo.); ATCC (American Type Culture Collection, Rockville, Md.); LTI (Life Technologies, Rockville, Md.); and Promega (Promega Corp., Madison, Wis.).

In the following methods, all solutions used in these methods were sterile (with the exception of TSH, controls, patient specimens) and treated aseptically. All manipulations were conducted in a biosafety cabinet under aseptic conditions. Cell culture media (e.g., Ham's F-12, EMEM, etc.) were obtained from LTI, while additive reagents such as non-essential amino acids were obtained from Sigma.

Freezer vials of cells should not be allowed to warm from their $-80°$ C. (or lower) storage temperature until immediately prior to thawing and use in the methods of the present invention, as cycling of the temperature may result in viability losses. Because it contains dithiothreitol, which is unstable at room temperatures, the 5× cell lysis solution should be removed from its $-20°$ C. storage temperature only long enough to remove the required volume for preparation of the 1× solution. As it also contains dithiothreitol, reconstituted luciferase substrate solution should be kept frozen at $-20°$ C. until just prior to use, at which time it may be removed and placed in a 25–37° C. water bath to thaw and reach room temperature.

In general, when removing liquid from wells (e.g., microtiter plates, etc.), the liquid may be dumped from the wells into a receptacle in a biosafety hood. The residual liquid can be drained and removed by placing the plate upside down on a sterile, absorbent wipe. Or, the liquid may be removed by aspiration using a fine tip on the aspirator. If aspiration is used, the plate is held at a steep angle so that the liquid does not overflow the wells, and the aspirator tip is directed down the side of the well almost to the bottom to remove the liquid and only leave minimal residue. However, care must be exercised in order to prevent disturbance of the cell monolayer, as the cells can be easily removed by the aspirator.

As indicated in the methods below, it is recommended that specimens, standards, and controls be run in triplicate. Because of the viscous nature of Solution 3 and the difficulty in achieving adequate mixing in the wells, the best reproducibility was achieved when the total triplicate volume is +10% (33 µl) of these reagents is transferred to the required triplicate volume+10% (330 µl) of Solution 3, thoroughly mixed, and 110 µl transferred to the triplicate wells.

In the preparation of cell monolayers (e.g., within the wells of microtiter plates), it is preferred that the cells be distributed evenly within the wells. Thus, in order to avoid uneven cell distributions, the transfer of cell suspensions into wells should be performed in a vibration-free biosafety hood. After all of the wells in a plate have received cells, the plate is covered and carefully placed on a solid, vibration-free surface, for 30 minutes, to allow the cells to attach undisturbed, to the bottom of the wells. This helps ensure that an even distribution of cells is present in each of the wells.

EXAMPLE 1

Preparation of CHO-Rluc Cells For Testing

In these experiments, CHO-Rluc cells were prepared from W-25 CHO—R cells for use in the testing methods to detect TSI in Graves' disease patients. Pools of puromycin-resistant cells were obtained and tested for light output in response to bovine TSH. Clones with the highest light output were selected for use in the experiments described below.

CHO-Rluc cells were grown in cell culture flasks (e.g., T-225 flasks) in growth medium containing Ham's F-12 medium, 10% FBS (heated at 56° C. for 30 minutes to inactivate complement), 2 mM glutamine, and 1× non-essential amino acids. The flasks were incubated at 35–37° C., in a humidified atmosphere, containing 5% carbon dioxide.

After the cell cultures reached confluence, the medium from each flask was aspirated, and the cell monolayers were washed with HBSS without $Ca^{++}$ and $Mg^{++}$. Then, 7 ml of a 0.25% trypsin/1 mM EDTA solution were added to each flask, and allowed to react with the monolayers for approximately 5–10 minutes at room temperature, in order to detach and disperse the cells in a nearly unicellular suspension. The cell suspensions were then centrifuged for approximately 5 minutes at 300–400×g. The supernatants were then removed and the pelleted cells resuspended in 8 ml of a medium prepared by mixing 4 ml EMEM containing 1×HBSS and 20% FBS with 4 ml of cryoprotective medium (EMEM containing 1×HBSS and 15% DMSO).

An aliquot of each cell suspension was then used to determine the number of cells present in the suspension. This determination can be accomplished using any method known in the art, including but not limited to methods using a hemocytometer to determine the cell count. Thus, it is contemplated that any method can be used to determine the cell count in the suspensions. Based on the number of cells in the suspension, the cells were aliquoted by volume to approximately $2 \times 10^6$ cells into standard freezer vials. The cells were then stored frozen at $-90°$ C. for short-term storage. For long-term storage, the cells were stored in liquid nitrogen (about $-200°$ C.).

EXAMPLE 2

CHO-Rluc Assay Plate Preparation and Testing

In these experiments, CHO-Rluc cells prepared as described in Example 1 were used in assays for diagnosis of Graves' disease. To prepare 24 monolayers for testing, 24 wells in a 96-well microtiter plate were first treated by adding 50–100 µL 0.1% gelatin solution (Sigma) to enhance attachment of the cells to the bottom of the 24 wells chosen for the test. Following incubation for approximately 1 minute at room ID temperature, the gelatin solution was removed from each of the wells by aspiration. It was noted that the gelatin can remain on the cells for longer than one minute. The gelatin serves to coat the wells with collagen, so that the cells attach more quickly to the wells and reach confluence more rapidly. However, cells can be planted and grown to confluence without gelatin and still perform well.

A freezer vial of CHO-Rluc cells produced as described in Example 1 was rapidly thawed in a 37° C. water bath to provide approximately 0.4 ml cell suspension, which was well-mixed using a pipette. The cells were then added to 2.5 ml GM (also referred to as "Planting Medium"), thoroughly mixed by vortexing for 1–2 seconds, and 100 µL aliquots of the cell suspension were added to each well, and the plates were covered. It is preferable to produce an even distribution of cells in each well. Thus, to avoid uneven cell distributions, the microtiter plate should be placed in a vibration-free hood for cell planting and attachment of cells to the walls of the microtiter plate. The planted cells were then incubated at 35–37° C., in a humidified atmosphere, containing 5% $CO_2$, for approximately 20–24 hours, to allow the cells to form a nearly or completely confluent monolayer.

The GM was then aspirated from each well as completely as possible, being careful not to disturb the monolayers (i.e., confluent monolayers remain in the wells). The monolayers were rinsed with approximately 100 μL Starvation Medium (HBSS containing $Ca^{++}$ (0.14 g/L) and $Mg^{++}$ (0.048 g/L) per well. The Starvation Medium was aspirated and a fresh 100 μL of Starvation Medium was then added to each well. It is important that these steps be conducted sufficiently rapidly that the cell monolayers do not dry. The plates were then incubated overnight in a 35–37° C., 5% $CO_2$, humidified incubator. Following incubation, the Starvation Medium was aspirated from the wells, using care to avoid disturbing the monolayers. Then, approximately 100 μL Stimulation Medium were added to each monolayer, again working quickly so that the monolayers did not dry.

Then, in an alternative method to that previously described, 10 μL of patient, control, and TSH standard solutions were added to the appropriate wells. The TSH standards and IgG samples were diluted with diluent (i.e., HBSS-NaCl+222 mM sucrose). The TSH standards were tested at concentrations of 0, 10, 100, 1000, and 5000 μIU. Patient samples were diluted to a concentration of 10 mg protein/ml for use in the assay. As the Stimulation Medium is viscous, thorough mixing of the suspensions was important. Adequacy of the mixing was ascertained by microscopic examination of the monolayers. The plates were incubated for 4 hours at 35–37° C. in a 5% $CO_2$, humidified incubator. The medium was carefully aspirated from each well and 150 μL lysis solution (Promega) was added to each well. The lysis solution contained 25 mM Tris-phosphate, pH 7.8, 2 mM diaminocyclohexane tetraacetic acid (CDTA), 2 mM dithiothreitol (DTT), 10% glycerol, and 1% Triton X-100. The plates were then incubated for 30 minutes at room temperature, to allow the monolayers to lyse. Following lysis, each well was scraped and stirred using a pipet tip. Then, 25 μL of lysate were removed from each well and placed in a luminometer tube (12×75 mm, polypropylene), and 50 μL of luciferase substrate (Promega) were then added. The tubes were vortexed for 1–2 seconds and the RLU/sec values determined, using settings of 5 seconds delay and 10 second read. To obtain average net values, the average of the "0 TSH" (i.e., the negative control) samples was subtracted from all test average values.

EXAMPLE 3

Preparation of IgG Samples

In these experiments, patients' IgG was prepared for testing in the present methods. Lyophilized IgG samples from 38 well-known and characterized, untreated Graves' disease patients were kindly provided by Dr. B. Y. Cho (Department of Internal Medicine, Seoul National University, College of Medicine, Seoul, Korea). As most of the samples had been previously tested in standard methods using CHO—R and FRTL-5 cells, these test results were known for 35 of these samples.

In preparation for lyophilization, the IgGs were affinity-purified using protein A-Sepharose CL-4B columns, as known in the art, and then dialyzed against 100 volumes of distilled water at 4° C. The dialysis water was changed every 8 hours over a 2 day period. After removal of denatured protein by centrifugation at 1500×g for 15 minutes at 4° C., the IgG was lyophilized and stored at −20° C. until used in the experiments described herein.

In some experiments, purified untreated Graves' IgG was diluted in normal serum (euthyroid sera discussed in Example 7, below), and assayed using the CHO-Rluc assay described below.

EXAMPLE 4

CHO-Rluc Assays

In these experiments, the performance of CHO-Rluc cells using the method described by Evans et al. (Evans et al., J. Clin. Endocrinol. Metabol., 84:374 [1999]) was evaluated. The media from the cell monolayers in the 24 wells used in the 96-well microtiter plates prepared as described in Example 2 were aspirated and replaced with 100 μL Ham's F-12 medium containing 10% charcoal-stripped calf serum (Sigma), and incubated overnight at 35–37° C., in a humidified atmosphere containing 5% $CO_2$.

Then, 10 μL of bovine TSH standards diluted to a range of concentrations (e.g., 0 10, 100, and 1000) and Graves' IgG (dissolved to a concentration of 10 mg protein/ml in charcoal-stripped calf serum) were added to respective quadruplicate wells. The suspension in each well was mixed, and the plates were incubated for 4 hours at 35–37° C., in a humidified atmosphere containing 5% $CO_2$. The medium was then aspirated from each of the wells, and 150 μL of lysis buffer (Promega, as described above) were added to each well. The plates were then incubated at room temperature for 30 minutes to allow lysis of the cells in the wells. Then, 25 μL of each lysate were transferred to a 12×75 polyethylene luminometer tube, to which 50 μL of luciferase substrate (Promega) were added immediately prior to mixing and reading in the luminometer at settings of 5 seconds delay and 10 second read. The luminometer read out provided results as relative light units per second (RLU/sec). The negative or "zero" TSH standard value was subtracted from each of the readings. In one run, the average net value for the zero μIU/ml TSI standard was 68,011 RLU/sec, while the result for the sample containing 10 μIU/μl was 4031 RLU/sec, the sample containing 1000 μIU was 222,801 RLU/sec, one Graves' IgG test sample was −384 RLU/sec (sample #1), and another Graves' IgG test sample was −3012 RLU/sec (sample #9).

The Graves' IgG sample #1 and sample #9 were previously assayed using standard FRTL-5 cells and a cAMP RIA assays. In the cAMP assay, values greater than 153 with FRTL-5 cells are considered positive for the presence of TSI. The cAMP value with FRTL-5 cells for sample #1 was 212, and the cAMP value for sample #9 was 803. The CHO—R values for these same samples (#1 and #9) were 116 and 1733, respectively, in an assay system where CHO—R values greater than 173 are considered to be positive for Graves' disease. Thus, these results clearly indicate that there is a discrepancy between the results obtained using different cell lines for the detection of Graves' disease. Indeed, the use of the Evans et al. method yielded negative results for both IgG samples, indicating that this system with CHO-Rluc is useless for detecting human TSI, despite the fact that the response to bovine TSH was very good.

Furthermore, during the development of the present invention (as described below), it was determined that if the CHO-Rluc cells were planted in a medium containing charcoal-stripped calf serum for 24 hours (i.e., to reach confluence), the cells simply attached to the bottom of the wells, but did not multiply and become confluent during the incubation period, unlike the situation in which normal FBS was used. Thus, this surprising result indicates that the use of charcoal-stripped serum in the medium resulted in a starvation step for the cells, somewhat analogous to the incubation of FRTL-5 cells in 5H medium.

In some experiments purified, untreated Graves' IgG diluted in normal serum, were tested in the CHO-Rluc assay (with PEG). For IgG #10, (2 mg/ml), the RLU/sec value was 131,461; for IgG#15 (2 mg/ml), the RLU/sec value was 180,327; for IgG#27 (5 mg/ml), the RLU/sec value was 179,777; and for IgG#32 (5 mg/ml), the RLU/sec value was 112,627. These results clearly show that the CHO-Rluc assay measures TSI in the presence of serum.

EXAMPLE 5

Development of Media Formulations

In view of the previously-described experiments, the effects of different media formulations were investigated for use with the CHO-Rluc cells in the measurement of bovine and human TSI. In these experiments, various media formulations were tested for the "starvation," and "stimulation" steps in the CHO-Rluc assay, using bTSH standards and IgG extracted from the sera of Graves' disease patients.

In these experiments, once the cell monolayers contained within the wells of 96-well microtiter plates (as described above), reached confluence, the Growth Medium was removed by aspiration and 100 μL of Starvation Medium were added to each monolayer. The plates were then incubated for 16–24 hours at 35–37° C., in a humidified atmosphere containing 5% $CO_2$, to starve or condition the cells. The Starvation Medium was then aspirated from the wells.

To perform the assay, 10 μL of the patient specimen IgG, bTSH standards, and IgG controls (normal and Graves' disease sera), were added to the monolayers in triplicate. The suspensions were mixed within each well, and incubated under the above conditions for 4 hours. The liquid was then removed from each monolayer by aspiration, and 150 μL of lysis buffer (Promega, as described above) were added to each well. The plates were allowed to incubate at room temperature for 30 minutes to lyse the cells in the monolayers.

In order to measure the amount of cell stimulation caused by the TSH standard or antibody to the TSH receptor, the luciferase in the cell lysates was measured by adding 25 μL of lysate to a luminometer tube to which 50 μL of substrate solution (Promega) were added. The suspensions were mixed and then read in a luminometer with settings of a 5 second delay and a 10 second read, to determine the RLU for each sample.

In order to use the cells for TSI or TSH stimulation, the Starvation Medium was removed by aspiration, and 100 μL of the Stimulation Medium were added to each well. This Stimulation Medium was HBSS-NaCl, with 222 mM sucrose. The following Table provides a comparison of the formulations of HBSS-NaCl+222 mM sucrose and standard HBSS.

TABLE 1

HBSS Medium Formulation Comparisons

| Component | HBSS-NaCl + 222 mM Sucrose (g/L) | Standard HBSS (g/L) |
| --- | --- | --- |
| $CaCl_2$ | 0.144 g/L | 0.14 g/L |
| KCl | 0.373 | 0.400 |

TABLE 1-continued

HBSS Medium Formulation Comparisons

| Component | HBSS-NaCl + 222 mM Sucrose (g/L) | Standard HBSS (g/L) |
| --- | --- | --- |
| $KH_2PO_4$ | 0.060 | 0.060 |
| $MgSO_4$ | 0.048 | 0.048 |
| $Na_2HPO_4$ | 0.097 | 0.048 |
| $NaHCO_3$ | 0.00 | 0.35 |
| NaCl | 0.00 | 8.00 |
| D-Glucose | 1.00 | 1.00 |
| Sucrose | 76.00 | 0.;00 |
| HEPES | 4.77 | 0.00 |
| Bovine Serum Albumin | 10.00 | 0.00 |

This Stimulation Medium formulation is a formulation that is commonly used in the measurement of TSI in FRTL-5 and CHO—R cells.

The results of experiments to test various Starvation Medium formulations are indicated in the following Table. In these experiments, the HBSS-NaCl+222 mM sucrose Stimulation Medium was used. As indicated in Table 2, the standard HBSS with 20 mM sucrose yielded the best signal to noise ratio (i.e., the lowest background and highest value for Graves' IgG).

TABLE 2

RLU/Sec Results for Various Starvation Media

| | RLU/Sec | | | |
| --- | --- | --- | --- | --- |
| Starvation Medium | 0 TSH | 10 μIU TSH/ml | 1000 μIU TSH/ml | #13 IgG |
| CHO GM* | (66,232) | 782 | 265,195 | 5144 |
| CHO Char** | (50,638) | 5602 | 229,492 | 34,042 |
| HBSS--NaCl + 222 mM Sucrose | (32,289) | 2188 | 142,666 | 30,640 |
| Standard HBSS with 20 mM Sucrose | (27,139) | 14390 | 156,548 | 53,994 |

*CHO GM is CHO Growth Medium containing 10% FBS.
**CHO Char. is CHO Growth Medium with 10% charcoal-stripped calf serum.

EXAMPLE 6

Use of PEG

As PEG may be used in in vitro antigen/antibody reactions to assist or enhance the reaction rate, a trial was conducted in which PEG was incorporated into the Stimulation Medium. As this compound may decrease the off-rate or dissociation of the antigen/antibody complex, the use of PEG in the methods of the present invention was investigated.

Preliminary results with 12% PEG-8000 (i.e., ave. MW 8,000) in HBSS-NaCl-sucrose, resulted in monolayers with increased spaces between the cells. To reduce this apparent osmotic stress, 6% PEG-8000 in HBSS-NaCl+111 mM sucrose was tested. In these experiments, the Starvation Medium yielding the best results (i.e., standard HBSS+20 mM sucrose) was used. The results are shown in Table 3, below.

TABLE 3

RLU/Sec Results for Stimulation Media With and Without PEG

| Stimulation Medium | RLU/Sec | | | |
|---|---|---|---|---|
| | 0 TSH | 10 µIU TSH/ml | 1000 µIU TSH/ml | #13 IgG |
| HBSS--NaCl + 222 mM Sucrose | (21,671) | 1336 | 82,466 | 39,082 |
| HBSS--NaCl + 111 mM Sucrose, +6% PEG-8000 | (32,562) | 5980 | 207,831 | 174,461 |

As indicated in Table 3, the incorporation of 6% PEG-8000 significantly and substantially enhanced the luminescent signal from the CHO-Rluc cells, in response to added bTSH, as well as Graves' IgG.

An additional experiment was conducted to determine the optimal concentration of PEG-8000 to use in the Stimulation Medium. The net values for one Graves' sample (Graves' IgG #20), with an FRTL-5 cAMP value of 957, are shown in Table 4. As indicated in this Table, 6% PEG yielded maximum signal for Graves' TSab.

TABLE 4

RLU/Sec Results for Various PEG Concentrations

| Results | % PEG in Stimulation Medium | | | | |
|---|---|---|---|---|---|
| | 2% | 4% | 6% | 8% | 10% |
| RLU/sec | 15,566 | 52,259 | 87,908 | 73,260 | 47,991 |

Subsequent experiments have shown that the Starvation Medium need not contain 20 mM sucrose, as there is no statistically significant difference in the results with or without it.

In addition, experiments were conducted to demonstrate that the assay of the present invention measures thyroid-stimulating immunoglobulin in a dose-dependent manner. In these experiments, three Graves' disease IgG samples (#6, #11, and #16) were tested. Serial 3-fold dilutions were made using the Stimulation Medium containing 6% PEG-8000, and the methods described above. The results are shown in FIG. 1, which shows the linearity of the dilutions. The IgG samples were prepared from 10 mg/ml stocks, which were then tested undiluted, and serially diluted (3-fold dilutions) to 0.3333, 0.1111, 0.0371, 0.0123, and 0.0041 dilutions (i.e., to yield 3.333 mg/ml, which was then diluted 3-fold to yield 1.111 mg/ml, etc.).

The FRTL-5 value for IgG sample #6 was 2080, while the FRTL-5 value for IgG sample #11 was 4453, and for IgG sample #16, the value was 830. The following Table lists the results for each of these samples. The correlation coefficients (r) were 0.857 for IgG sample #6, 0.858 for sample #11, and 0.995 for sample #16.

TABLE 5

Dose-Response (Dilution) Curves of Graves' IgG Specimens*

| Sample | Dilution Factor | | | | | |
|---|---|---|---|---|---|---|
| | 1 | 0.3333 | 0.1111 | 0.0371 | 0.0123 | 0.0041 |
| IgG #6 | 176,123 | 159,694 | 62,115 | 13,480 | −6,628 | −2,574 |
| IgG #11 | Not Done | 368,373 | 324,143 | 158,641 | 77,298 | 30,166 |
| IgG #16 | 222,413 | 90,646 | 40,048 | 8,093 | −1,705 | −691 |

*All values are reported as RLU/sec.

EXAMPLE 7

Alternative Protocol Using PEG

In these experiments, alternative protocols using PEG were tested. First, freezer vials of CHO-RLuc cells were thawed, diluted in Growth Medium (the contents of each cell vial were added to 2.5 ml medium), and 100 µl of this cell suspension were added 10 each of the 24 gelatin-coated wells of a 96-well microtiter plate, prepared as described previously. The plates were incubated for 20–24 hours in a 35–37° C., humidified incubator with an atmosphere containing 5% $CO_2$. This provided monolayers that were loosely confluent.

The Growth Medium was removed and the monolayers rinsed with 100 µl of Starvation Medium (normal HBSS with $Ca^{++}$ and $Mg^{++}$), and a final 100 µl were added to each monolayer before incubating overnight under the conditions described above. Following incubation, the Starvation Medium was removed and 100 µl of Stimulation Medium containing 6% PEG (i.e., as described above) were added to each monolayer. Then, 10 µl of each of the standards and samples were placed into the wells (in triplicate). While other volumes were tested (e.g., 25 µl, 50 µl and 75 µl), the values obtained were substantially equivalent to those obtained with 10 µl volumes. Thus, the smaller volume was used in order to conserve the samples and reagents, and to minimize the concentration of potentially interfering substances present in some serum samples.

The well contents were mixed and the monolayers incubated as described above for 4 hours (i.e., a stimulation step). The medium was removed from each well, and 150 µl of lysis solution (as described above) were added to each well. The monolayers were allowed to stand at room temperature for 30 minutes for lysis to occur. Then, 25 µl of each lysate were added to individual luminometer tubes. Fifty microliters of luciferase substrate (as described above) were added to each tube, the contents mixed, and the tubes immediately read in a luminometer with settings of 5 seconds delay and a 10 second read time.

Figure 6:
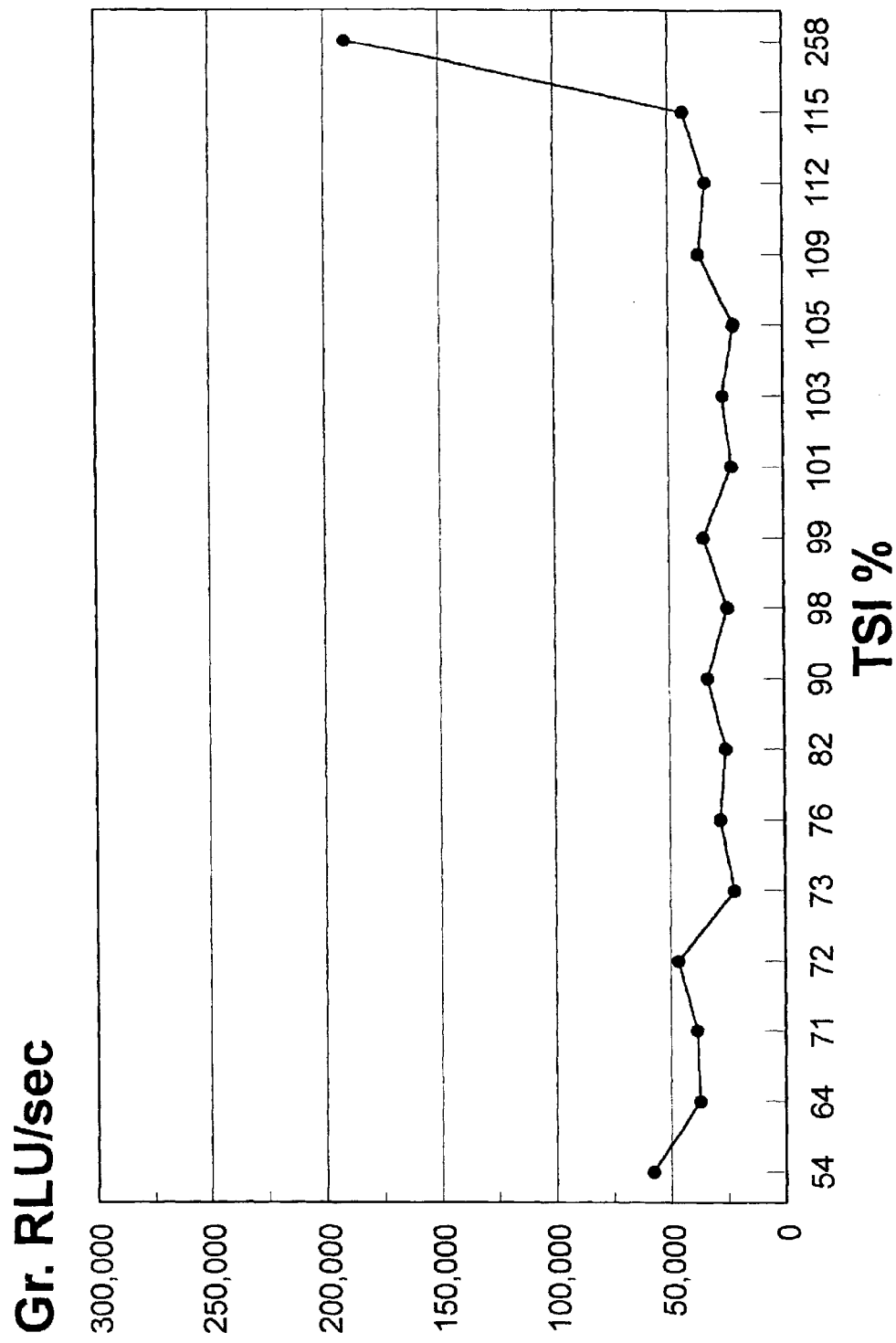
FIG. 6 shows the results for a group of samples with known TSI results using FRTL-5 cells (10 µl samples of LCA TSI specimens).

In an experiment to determine the normal range of euthyroid sera, 24 specimens obtained from a reference laboratory were run using the CHO-Rluc assay as described above. The sera were euthyroid in that none of the samples were submitted for thyroid testing. The mean (55,334 RLU/sec) and standard deviation (1 SD=7,434 RLU/sec) were calculated for these 24 euthyroid samples. The results are shown in FIG. 6. The SD value was then multiplied by three, which yielded a cut-off for normal, non-Graves' disease values of 77,636 RLU/sec. This cut-off encompasses >99% of the normal population; values greater than this were considered to be TSI positive.

Figure 7:
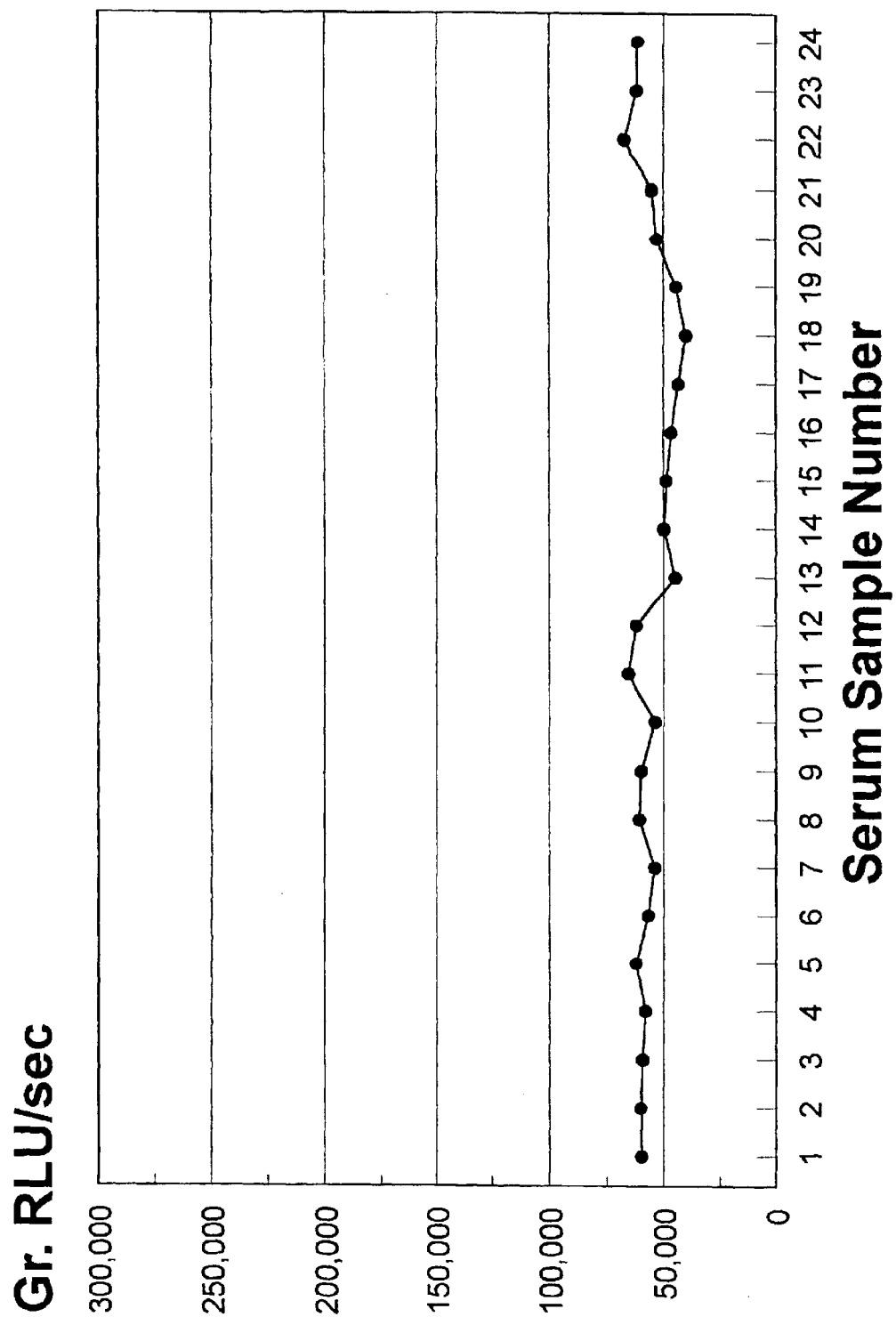
FIG. 7 shows the results for a group of normal samples (10 µl of AML "normal" specimens).

In a separate set of experiments, a group of 17 patient specimens which previously been tested by a commercial esoteric testing laboratory using cAMP RIA and FRTL-5 cells for TSI, were tested using the CHO-Rluc cells with the above procedure. The FRTL-5 test results indicated 16 of the patient specimens were negative for TSI (i.e., only one was positive). The single positive specimen identified by the FRTL-5/cAMP assay (258% or 1.98× the cut-off, where the assay cut-off was 130%), was likewise positive by the CHO-Rluc assay (190,691 RLU/sec) based on a 2.45× cut-off of 77,636 RLU/sec, as shown in FIG. 7. The CHO-Rluc values of the 16 patient specimens which were negative (i.e., normal) by the FRTL-5/cAMP assay were found to be in good agreement with the 24 normal sera used to establish the normal range for the assay (See, FIG. 6).

EXAMPLE 8

Comparison of RHO-Rluc Method and Standard Methods

In these experiments, the methods of the present invention utilizing Stimulation Medium containing 6% PEG-8000 were compared with methods using the standard HBSS-containing Starvation Medium and Stimulation Medium, to obtain luciferase values for 35 of the untreated Graves' disease IgG specimens obtained from Dr. Cho.

Figure 4:
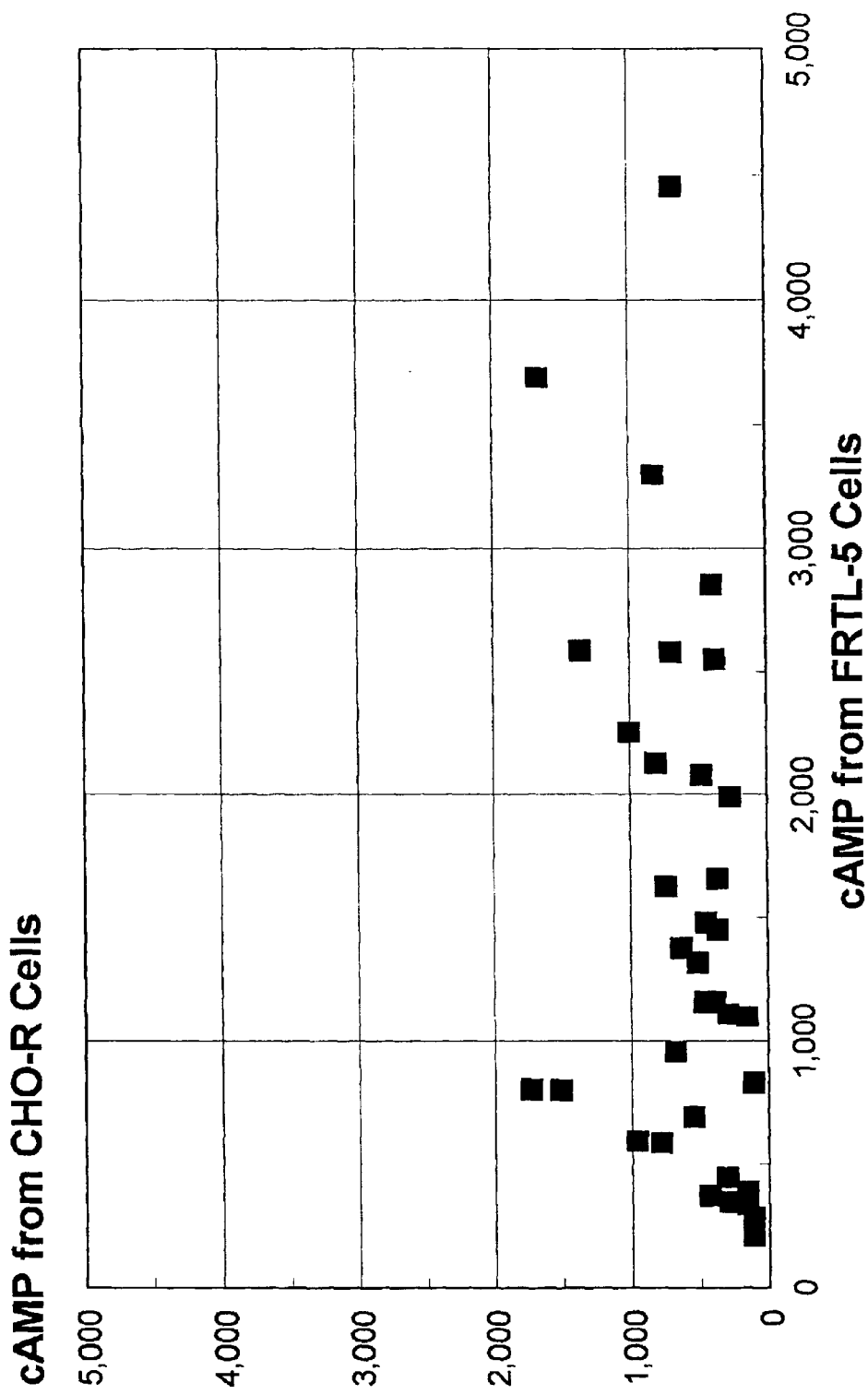
FIG. 4 provides a comparison of CHO—R cAMP results with FRTL-5 cAMP results for IgGs from 35 untreated Graves' patients.
Figure 5:
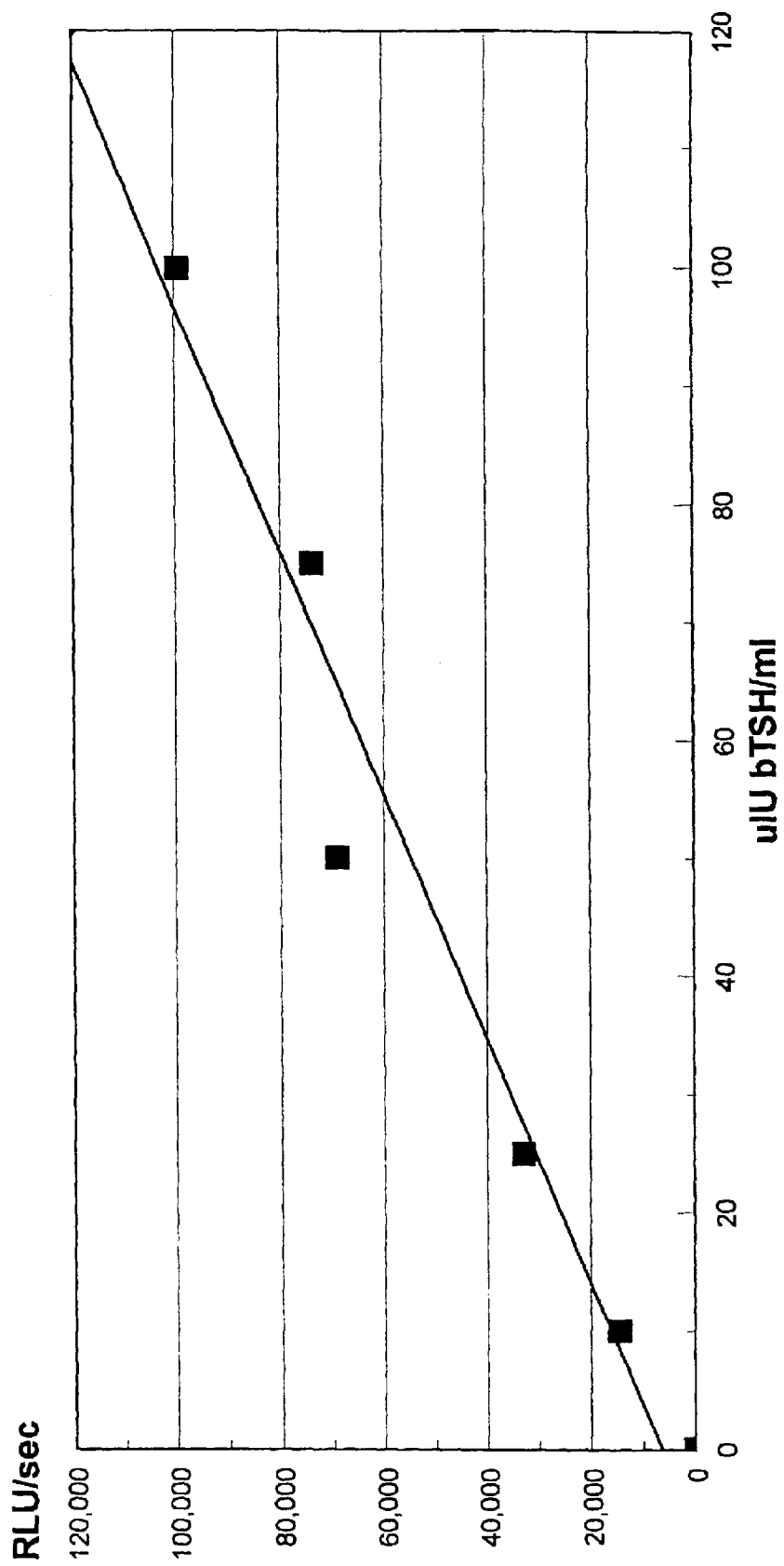
FIG. 5 shows the linearity of the response to bTSH of the CHO-Rluc cells.

The cAMP values obtained by Dr. Cho with FRTL-5 and CHO—R cells using the same IgG samples as used in methods of the present invention are shown in comparison with the CHO—R luciferase results in FIGS. 2, 3 and 4. FIG. 5 shows the linearity of luciferase response to bTSH.

Figure 2:
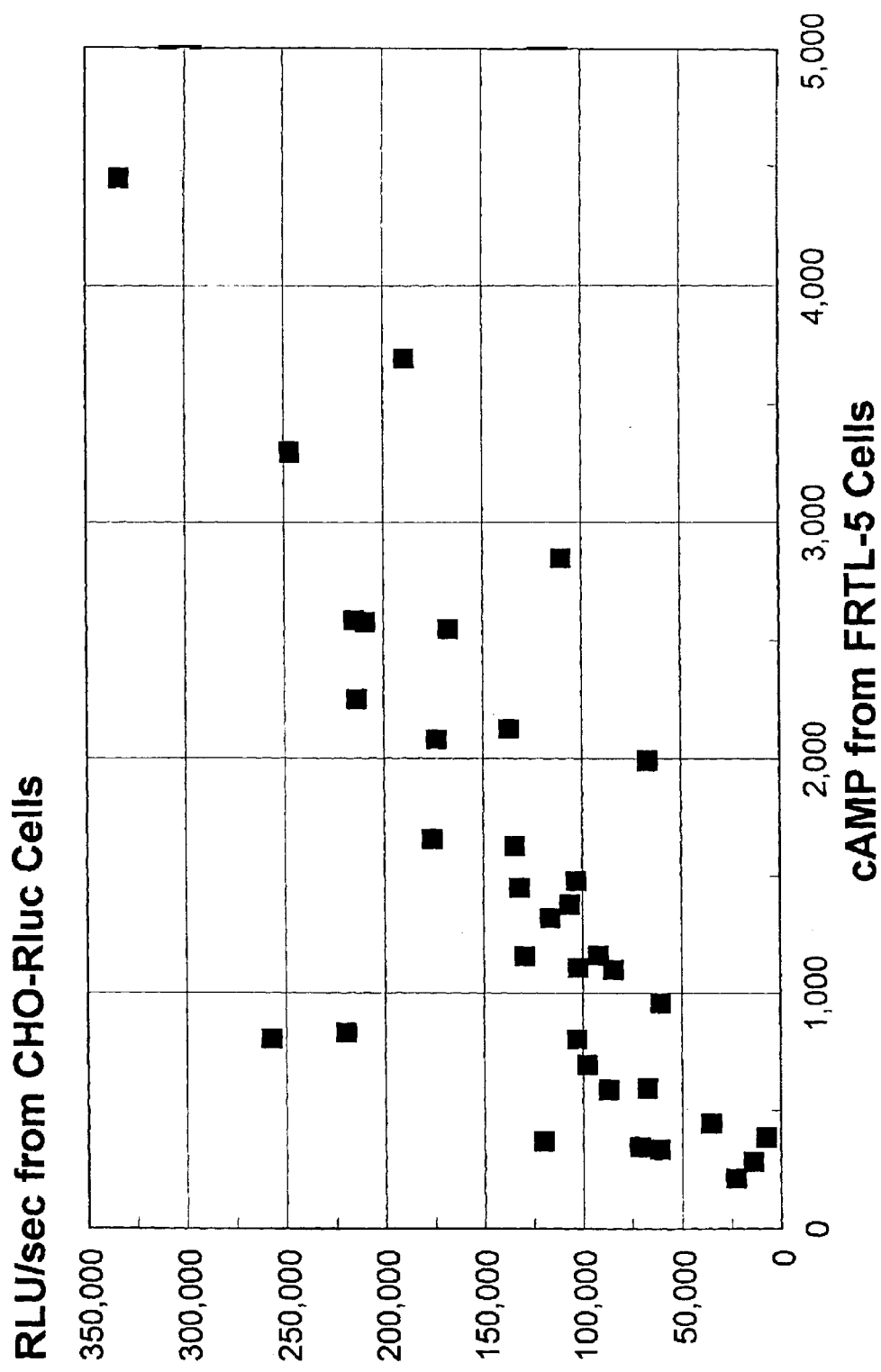
FIG. 2 provides a comparison of CHO-Rluc luciferase results with the FRTL-5 cAMP results for IgGs from 35 untreated Graves' patients.
Figure 3:
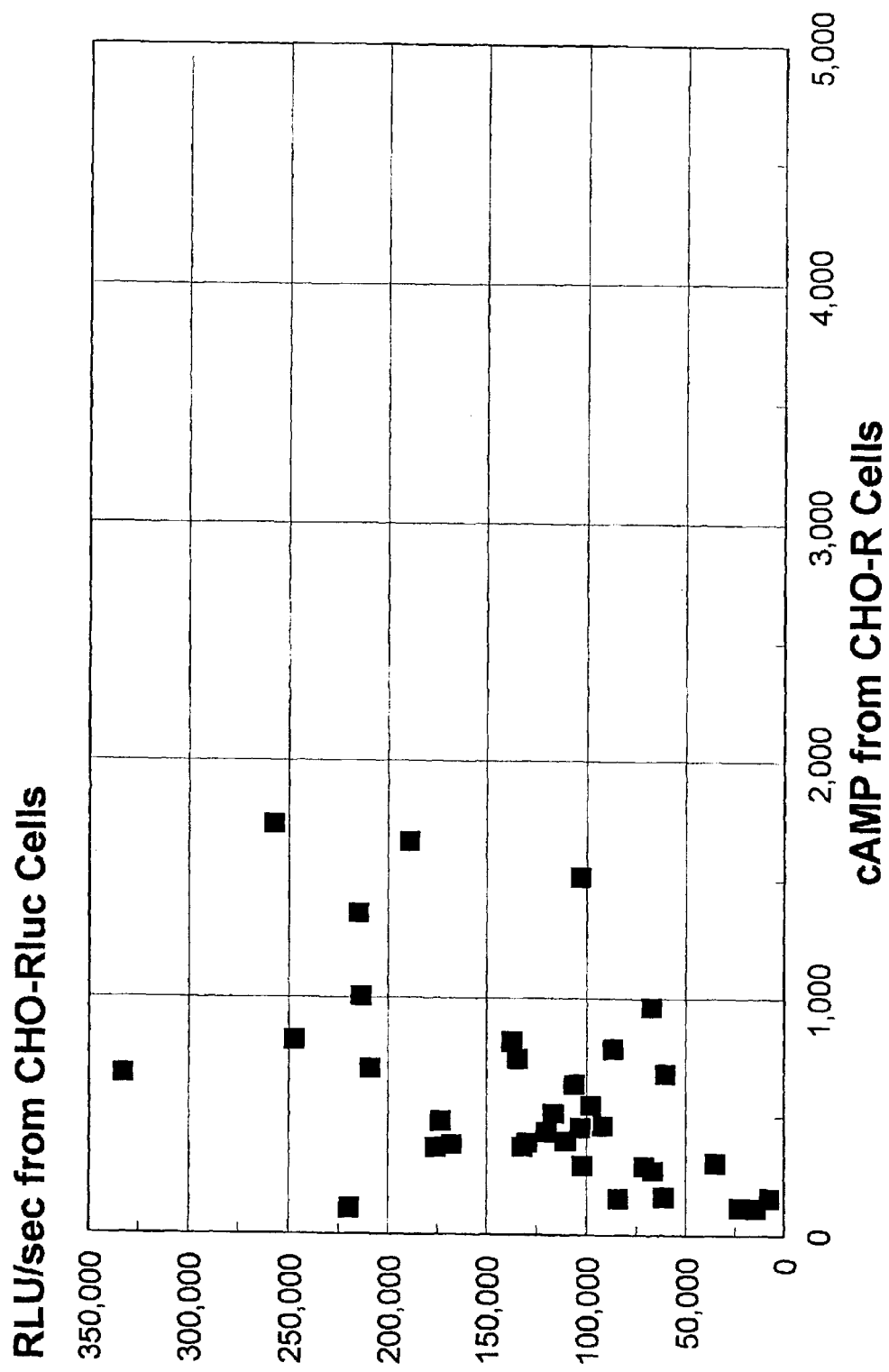
FIG. 3 provides a comparison of CHO-Rluc luciferase results with CHO-R cAMP results for IgGs from 35 untreated Graves' patients.

FIG. 2 provides a comparison of CHO-Rluc luciferase results with the FRTL-5 cAMP results. This Figure indicates that the correlation between these methods is quite good. FIG. 3 provides a comparison of CHO-Rluc luciferase results with CHO—R cAMP results. The CHO—R CAMP cut-off value was 173. Values below this cutoff were as follows (CHOluc RLU/sec): 110 (219,913), 113 (14,434), 116 (25,373), 152 (84,493), 156 (7576), and 161 (61,321). As indicated in this Figure, the range of CHO—R cAMP results is relatively narrow, as compared with the CHO-Rluc values. This is also shown in FIG. 4, which provides a comparison of CHO-R cAMP results with FRTL-5 cAMP results. The CHO—R value was 173. The FRTL-5 cut-off value was 153. Values below cutoff were as follows (FRTL-5 values): 110 (830), 113 (283), 116 (212), 152 (1100), 156 (388), and 161 (335). The average+/−SD values for the IgG Control (ICN), for the tests shown in FIG. 2 were 472+/−4015 (n=8).

FIG. 5 shows the linearity of the response to bTSH of the CHO-Rluc cells. In these experiments, dilutions of bTSH were tested. The RLU/sec values obtained are shown in Table 6, below.

TABLE 6

Results for bTSH Dilutions

| | $\mu$IU TSH/ml | | | | |
|---|---|---|---|---|---|
| Results | 0 | 10 | 25 | 50 | 75 | 100 |
| RLU/sec | 0 | 5,921 | 20,227 | 34,426 | 54,396 | 62,206 |

It is contemplated that this linearity and sensitivity of response to bTSH will prove useful in the detection of blocking antibodies to the TSH receptor (e.g., those autoantibodies in patents with atrophic thyroiditis and Hashimoto's thyroiditis which block the TSH receptor, thereby preventing thyroid hormone production and release resulting in hypothyroidism). This Figure also provides at least a partial explanation of why the CHO—R cell line is not as sensitive to TSI from Graves' disease patients sera as the FRTL-5 cell line. In these results, the correlation coefficient (r) was 0.9925. The three S.D. (standard deviations) sensitivity was 1.3 $\mu$IU TSH/ml.

EXAMPLE 9

Monitoring of Immune Responses

In these experiments, the immune response of vaccine recipients is measured and monitored. Although it is not intended that the present invention be so limited, this Example describes the monitoring of a subject's immune response to herpes simplex (HSV) vaccine.

Prior to administration of vaccine, a serum sample (i.e., preimmune serum) is collected from the subject for use as a baseline or control, and stored frozen until testing. Serum samples are also collected at periodic intervals following administration of the vaccine (e.g., 1–2 weeks, 1 month, 2 months post-vaccination, etc.). The sera are thawed as necessary, and used in an assay to determine the presence and quantity (i.e., titer) of neutralizing antibodies. Sera are serially diluted and mixed with known quantities of HSV. These samples are diluted in diluent comprising Eagle's MEM with HBSS containing 2 mM glutamine, 2% FBS, and PEG (e.g., 6% PEG 8000). However, it is also contemplated that other diluents will find use in the present method, including diluents containing different concentrations and types of PEG, as appropriate for the virus and assay system used). These samples are added to cell monolayers containing cells capable of producing an enzyme such as β-galactosidase upon infection with HSV (e.g., ELVIS™ cells, Diagnostic Hybrids). Following overnight incubation under standard cell culture conditions, the monolayers are lysed and the enzyme activity is measured using chromogenic or luminogenic methods.

A positive response to the vaccine is indicated by the lowest dilution of post-vaccination serum which neutralizes HSV in the sample (i.e., as indicated by a low OD or luminescence value, in comparison with the preimmune control).

In summary, the present invention provides numerous advances and advantages over the prior art, including the avoidance of radioactivity, in combination with the advantages of ease of use, reliability, sensitivity, specificity, cost-effectiveness, and reproducibility.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostics, cell culture, and/or related fields are intended to be within the scope of the following claims.

What is claimed is:

1. A method for determining the presence of thyroid-stimulating antibodies in a test sample, comprising:
   a) providing:
      i) a test sample suspected of containing thyroid-stimulating antibodies,
      ii) CHO-Rluc cells comprising a reporter gene, and
      iii) polyethylene glycol;
   b) exposing said test sample to said cells and said polyethylene glycol under conditions such that said reporter gene is expressed; and
   c) observing increased expression of said reporter gene in said cells in the presence of said test sample compared to in the absence of said test sample, thereby detecting the presence of thyroid-stimulating antibodies.

2. The method of claim 1, wherein said observing is conducted using a luminometer.

3. The method of claim 1, wherein said observing further comprises measuring cyclic adenosine monophosphate concentration.

4. The method of claim 1, wherein said CHO-Rluc cells are cultured in Growth Medium.

5. The method of claim 1, wherein said CHO-Rluc cells are cultured in Stimulation Medium.

6. The method of claim 4, wherein said cells are exposed to said Growth Medium prior to exposure of said test sample.

7. The method of claim 5, wherein said cells are exposed to said Stimulation Medium after exposure to said test sample.

8. The method of claim 7, wherein said Stimulation Medium comprises said polyethylene glycol.

9. A method for determining the presence of thyroid-stimulating antibodies in a test sample, comprising:
   a) providing:
      i) a test sample suspected of containing thyroid-stimulating antibodies,
      ii) CHO-Rluc cells comprising a reporter gene, and
      iii) polyethylene glycol;
   b) exposing said test sample to said cells and said polyethylene glycol under conditions such that said reporter gene is expressed; and
   c) observing increased expression of said reporter gene in said cells in the presence of said test sample compared to in the absence of said test sample, thereby detecting the presence of thyroid-stimulating antibodies, wherein said observing utilizes a luminometer.

10. The method of claim 9, wherein said CHO-Rluc cells are cultured in Growth Medium.

11. The method of claim 9, wherein said CHO-Rluc cells are cultured in Stimulation Medium.

12. The method of claim 10, wherein said cells are exposed to said Growth Medium prior to exposure of said test sample.

13. The method of claim 11, wherein said cells are exposed to said Stimulation Medium after exposure to said test sample.

14. The method of claim 13, wherein said Stimulation Medium comprises said polyethylene glycol.

15. A method for determining the presence of thyroid-stimulating antibodies in a test sample, comprising:
   a) providing:
      i) a test sample suspected of containing thyroid-stimulating antibodies,
      ii) CHO-Rluc cells comprising a reporter gene,
      iii) Growth Medium, and
      iv) Stimulation Medium, wherein said Stimulation Medium comprises polyethylene glycol;
   b) exposing said cells to said Growth Medium to produce grown cells;
   c) exposing said test sample to said grown cells and said Stimulation Medium under conditions such that said reporter gene is expressed; and
   d) observing increased expression of said reporter gene in said cells in the presence of said test sample compared to in the absence of said test sample, thereby detecting the presence of thyroid-stimulating antibodies, wherein said observing utilizes a luminometer.

16. The method of claim 15, wherein said observing further comprises measuring the cyclic adenosine monophosphate concentration.

17. A method for determining the presence of thyroid-stimulating antibodies in a test sample, comprising:
   a) providing:
      i) a test sample suspected of containing thyroid-stimulating antibodies,
      ii) CHO-Rluc cells comprising a reporter gene, and
      iii) polyethylene glycol;
   b) exposing said CHO-Rluc cells to said test sample and to said polyethylene glycol under conditions such that said reporter gene is expressed; and
   c) observing increased expression of said reporter gene in said cells in the presence of said test sample compared to in the absence of said test sample, thereby detecting the presence of thyroid-stimulating antibodies, wherein luciferase activity in a control sample comprising CHO-Rluc cells exposed to bovine thyroid stimulating hormone is higher in the presence of polyethylene glycol than in the absence of said polyethylene glycol.

18. A method for determining the presence of thyroid-stimulating antibodies in a test sample, comprising:
   a) providing:
      i) a test sample suspected of containing thyroid-stimulating antibodies,
      ii) CHO-Rluc cells comprising a reporter gene, and
      iii) polyethylene glycol;
   b) exposing said CHO-Rluc cells to said test sample and to said polyethylene glycol under conditions such that said reporter gene is expressed; and
   c) observing increased expression of said reporter gene in said cells in the presence of said test sample compared to in the absence of said test sample, thereby detecting the presence of thyroid-stimulating antibodies, wherein said observing utilizes a luminometer, and wherein luciferase activity in a control sample comprising CHO-Rluc cells exposed to bovine thyroid stimulating hormone is higher in the presence of polyethylene glycol than in the absence of said polyethylene glycol.

19. A method for determining the presence of thyroid-stimulating antibodies in a test sample, comprising:
   a) providing:
      i) a test sample suspected of containing thyroid-stimulating antibodies,
      ii) CHO-Rluc cells comprising a reporter gene,
      iii) Growth Medium, and
      iv) Stimulation Medium, wherein said Stimulation Medium comprises polyethylene glycol;
   b) exposing said cells to said Growth Medium to produce grown cells;
   c) exposing said grown cells to said test sample and to said Stimulation Medium under conditions such that said reporter gene is expressed, and d) observing increased expression of said reporter gene in said cells in the presence of said test sample compared to in the absence of said test sample, thereby detecting the presence of thyroid-stimulating antibodies, wherein said observing utilizes a luminometer, and wherein luciferase activity in a control sample comprising CHO-Rluc cells exposed to bovine thyroid stimulating hormone is higher in the presence of polyethylene glycol than in the absence of said polyethylene glycol.

20. The method of claim 17, wherein said observing is conducted using a luminometer.

21. The method of claim 17, wherein said observing further comprises measuring cyclic adenosine monophosphate concentration.

22. The method of claim 17, wherein said CHO-Rluc cells are cultured in Growth Medium.

23. The method of claim 17, wherein said CHO-Rluc cells are cultured in Stimulation Medium.

24. The method of claim 22, wherein said cells are exposed to said Growth Medium prior to exposure of said test sample.

25. The method of claim 23, wherein said cells are exposed to said Stimulation Medium after exposure to said test sample.

26. The method of claim 25, wherein said Stimulation Medium comprises said polyethylene glycol.

27. The method of claim 18, wherein said CHO-Rluc cells are cultured in Growth Medium.

28. The method of claim 18, wherein said CHO-Rluc cells are cultured in Stimulation Medium.

29. The method of claim 27, wherein said cells are exposed to said Growth Medium prior to exposure of said test sample.

30. The method of claim 28, wherein said cells are exposed to said Stimulation Medium after exposure to said test sample.

31. The method of claim 30, wherein said Stimulation Medium comprises said polyethylene glycol.

32. The method of claim 19, wherein said observing further comprises measuring the cyclic adenosine monophosphate concentration.

* * * * *